United States Patent [19]

Mohacsi et al.

[11] Patent Number: 4,808,580
[45] Date of Patent: Feb. 28, 1989

[54] NAPHTHO[1,2-b][1,4]THIAZEPIN-4(5H)-ONES AND USE THEREOF IN TREATMENT OF ISCHEMIA AND BLOOD PRESSURE LOWERING

[75] Inventors: Erno Mohacsi, Summit; Jay P. O'Brien, Cedar Grove, both of N.J.

[73] Assignee: Hoffmann-La Roche Inc., Nutley, N.J.

[21] Appl. No.: 134,282

[22] Filed: Dec. 17, 1987

[51] Int. Cl.$^4$ ................ A61K 31/33; C07D 281/14
[52] U.S. Cl. .................................. 514/211; 540/488
[58] Field of Search ................ 540/491, 488; 514/211

[56] References Cited

U.S. PATENT DOCUMENTS

| | | | |
|---|---|---|---|
| 3,562,257 | 2/1971 | Kugita et al. | 540/488 |
| 4,438,035 | 3/1984 | Gaino et al. | 540/488 |
| 4,490,292 | 12/1984 | Maki et al. | 540/488 |
| 4,547,495 | 10/1985 | Maiorana et al. | 540/488 |
| 4,566,995 | 1/1986 | Simonovitch et al. | 540/488 |
| 4,567,175 | 1/1986 | Takeda et al. | 540/488 |
| 4,652,561 | 3/1987 | Mohacsi et al. | 540/488 |

OTHER PUBLICATIONS

Kugita et al., Chem. Pharm. Bull. 18 (10) 2028–2037 (1970).
Kugita et al., Chem. Pharm. Bull. 19 595–602 (1971).
Meshi et al., Chem. Pharm. Bull. 19 (8) 1546–1556 (1971).
Sato et al., Arzneim-Forsch. (Drug. Res.) Jahrgant 21 Nr. 9 (1971) 1338–1342.
Inoue et al., Chem. Soc. Perkin Trans. I (1984) 1725–1732.
CA 71(15): 70657j (1969).
CA 77(1): 5554h (1972).
CA 75(9): 63848b (1971).
CA 75(5): 36165v (1971).
CA 74(25): 141721a (1971).
CA 78(19): 119419u (1973).
CA 75(9): 61652j (1971).
CA 97(18): 150634b (1982).
CA 77(1): 105c (1972).
CA 76(11): 59674v (1972).
CA 76(15): 85854y (1972).
CA 78(11): 66993t (1973).
CA 93(21): 197787m (1980).
CA 79(11): 66331w (1973).
CA 87(19): 145450c (1977).
CA 97(25): 208153n (1982).
CA 83(7): 58901z (1975).
CA 90(3): 23002z (1979).
CA 90(17): 137874r (1979).
CA 93(23): 215403q (1980).
CA 97(21): 174401z (1982).
CA 96(18): 149164w (1982).
Inoue et al., Chem. Pharm. Bull. 33 (3) 1256–1259 (1985).
CA 73(13): 66641y (1970).

Primary Examiner—Mary C. Lee
Assistant Examiner—Robert C. Whittenbaugh
Attorney, Agent, or Firm—Jon S. Saxe; Bernard S. Leon; Matthew Boxer

[57] ABSTRACT

Compounds of the formula:

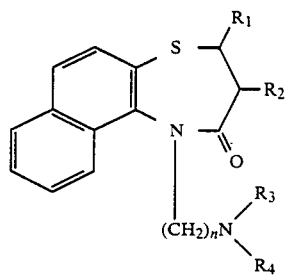

wherein $R_1$ is phenyl substituted with 1 to 3 substituents selected from the group consisting of lower alkoxy and halogen; $R_2$ is hydroxy, lower alkoxy, lower alkanoyloxy, lower cycloalkylcarbonyloxy;

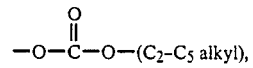

or

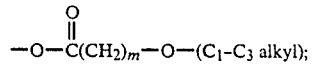

$R_3$ and $R_4$ are independently lower alkyl, phenyl lower alkyl or together form a piperidine or pyrrolidine ring; n is 2 to 4; m is 1 to 2; or pharmaceutically acceptable acid addition salts thereof are described. The compounds of formula I have activity as calcium channel blockers and accordingly, are useful as agents for lowering blood pressure, and as agents for treating ischemia.

38 Claims, No Drawings

NAPHTHO[1,2-B][1,4]THIAZEPIN-4(5H)-ONES AND USE THEREOF IN TREATMENT OF ISCHEMIA AND BLOOD PRESSURE LOWERING

BRIEF SUMMARY OF THE INVENTION

The invention relates to compounds of the formula

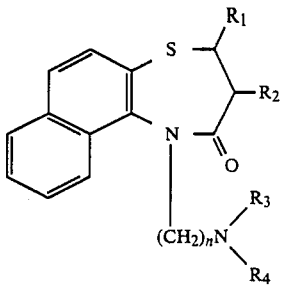

wherein $R_1$ is phenyl with 1 to 3 substituents selected from the group consisting of lower alkoxy and halogen; $R_2$ is hydroxy, lower alkoxy, lower alkanoyloxy, lower cycloalkylcarbonyloxy,

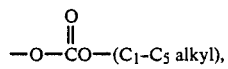

or

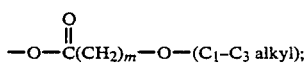

$R_3$ and $R_4$ are independently lower alkyl, phenyl lower alkyl or together form a piperidine or pyrrolidine ring; n is 2 to 4; m is 1 to 2; and pharmaceutically acceptable acid additions salts thereof.

The compounds of formula I are active as calcium channel blockers, and accordingly are useful as agents for treating ischemia and as agents for lowering blood pressure.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, and the like. Alternatively, the number of carbon atoms in an alkyl group is designated herein as in "$C_1$-$C_3$ alkyl" which denotes a straight or branched chain alkyl group containing 1 to 3 carbon atoms. The term "lower alkoxy" denotes a straight or branched chain lower alkoxy group containing 1 to 4 carbon atoms, for example, methoxy, ethoxy, propoxy, isopropoxy, butoxy, and the like. The term "halogen" denotes the halogens, that is, bromine, chlorine, fluorine and iodine. The term "lower alkanoyloxy" denotes a straight or branched chain alkanoyloxy group of 2 to 5 carbon atoms, for example, acetyloxy, propionyloxy, butyryloxy, isopropionyloxy and the like. The term "lower cycloalkyl" denotes a lower cycloalkyl group containing 3 to 6 carbon atoms, for example, cyclopropyl, cyclobutyl, cyclopentyl, and cyclohexyl. The term "phenyl lower alkyl" denotes a lower alkyl substituted by a phenyl, for example, phenylmethyl, phenylethyl, phenylpropyl, phenylbutyl and the like. The compounds of formula I are active as calcium antagonists, that is, calcium channel blockers, and accordingly, are useful as agents for lowering blood pressure and as agents for the treatment of ischemia.

The invention relates to compounds of the formula

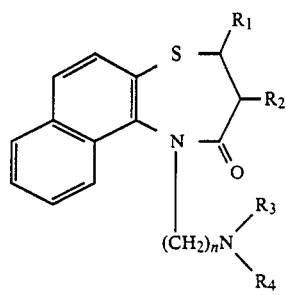

wherein $R_1$ is phenyl with 1 to 3 substituents selected from the group consisting of lower alkoxy and halogen; $R_2$ is hydroxy, lower alkoxy, lower alkanoyloxy, lower cycloalkylcarbonyloxy,

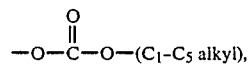

or

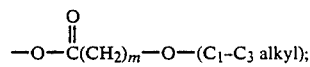

$R_3$ and $R_4$ are independently lower alkyl, phenyl lower alkyl or together form a piperidine or pyrrolidine ring; n is 2 to 4; and m is 1 to 2; and pharmaceutically acceptable acid addition salts thereof.

As used in the formulas herein a solid line (—■) indicates a substituent that is above the plane of the sulfur and nitrogen containing ring, a dotted line ( ||||||| ) indicates a substituent that is below the plane of the sulfur and nitrogen containing ring.

The compounds of formula I contain 2 asymmetric centers at the 2- and 3-positions. Accordingly, the compounds of formula I can be stereoisomers, that is cis or trans isomers.

As used herein, the term "cis" denotes a compound wherein the $R_1$ and $R_2$ substituents are both on the same side of the plane of the sulfur and nitrogen containing ring. As used herein the term "(+)-cis" denotes an enantiomer having an absolute configuration analogous to that of (2S,3S)-3-(acetyloxy)-2,3-dihydro-5-[2-(dimethylamino)ethyl]-2-(4-methoxyphenyl)naphtho[2,1-b][1,4]thiazepin-4(5H)-one, which is a (+)-cis compound of the invention.

A compound of the formula

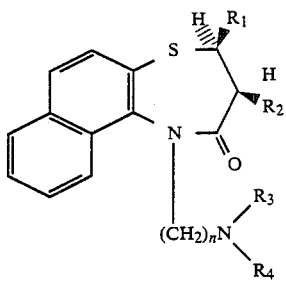   I′ wherein $R_1$, $R_2$, $R_3$, $R_4$ and n are as described above is a (+)-cis compound of the invention.

A compound of the formula

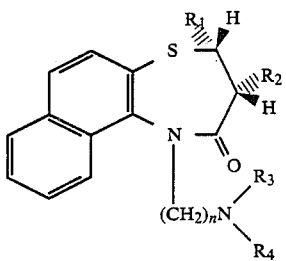   I″ wherein $R_1$, $R_2$, $R_3$, $R_4$ and n are as described above is the enantiomer of a compound of formula I′ and a (−)-cis compound of the invention.

Preferred compounds of the invention are cis compounds.

Especially preferred compounds of the invention are (+)-cis compounds.

As used herein the term "trans" denotes a compound of formula I wherein the $R_1$ and $R_2$ substituents are on opposite sides of the plane of the sulfur and nitrogen containing ring.

A compound of the formula

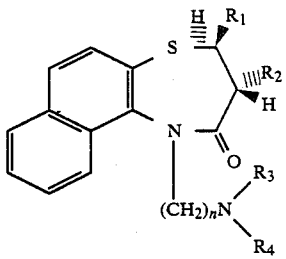   I‴ wherein $R_1$, $R_2$, $R_3$, $R_4$, and n are as described above is a trans compound of the invention.

A compound of the formula

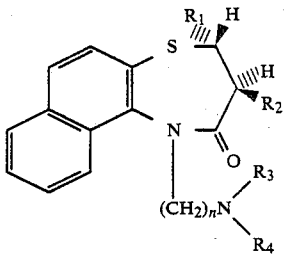   I^{IV} wherein $R_1$, $R_2$, $R_3$, $R_4$, and n are as described above is the enantiomer of a compound of formula I‴, and another trans compound of the invention.

Preferred compounds of formula I are those wherein $R_1$ is 4-lower alkoxyphenyl and $R_2$ is lower alkoxy. Of these, as has been pointed out above, cis compounds are preferred and (+)-cis compounds are especially preferred.

Other preferred compounds of formula I are those wherein $R_1$ is 4-lower alkoxyphenyl and $R_2$ is

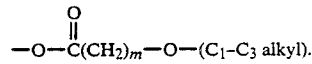

Of these, as has been pointed out above, cis compounds are preferred and (+)-cis compounds are especially preferred.

Yet other preferred compounds of formula I are those wherein $R_1$ is 4-lower alkoxyphenyl and $R_2$ is lower cycloalkylcarbonyloxy. Of these, as has been pointed out above, cis compounds are preferred and (+)-cis compounds are especially preferred.

Still other preferred compounds of formula I are those wherein $R_1$ is 4-lower alkoxyphenyl and $R_2$ is

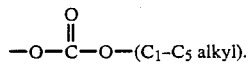

Of these, as has been pointed out above, cis compounds are preferred and (+)-cis compounds are especially preferred.

Other preferred compounds of formula I are those wherein $R_1$ is 4-lower alkoxyphenyl, $R_2$ is hydroxy or lower alkanoyloxy, $R_3$ is phenyl lower alkyl, $R_4$ is lower alkyl and n is 2 to 3. Of these, as has been pointed out above, cis compounds are preferred and (+)-cis compounds are especially preferred.

Preferred compounds of formula I are those wherein $R_1$ is 4-lower alkoxyphenyl; $R_2$ is lower alkanoyloxy; n is 2 to 3; and $R_3$ and $R_4$ are each independently lower alkyl. Of these, as has been pointed out above, cis compounds are preferred and (+)-cis compounds are especially preferred.

More preferred compounds of formula I are those wherein $R_1$ is 4-ethoxyphenyl, or more preferably 4-methoxyphenyl; $R_2$ is propionyloxy or more preferably hydroxy or acetyloxy; n is 2; and $R_3$ and $R_4$ are each ethyl or more preferably are each methyl. Of these, as has been pointed above, cis compounds are preferred and (+)-cis compounds are especially preferred. Exemplary of compounds of formula I are:

trans-rac-2,3-dihydro-3-hydroxy-5-[2-(dimethylamino)ethyl]-2-(4-methoxyphenyl)naphtho[2,1-b][1,4]thiazepin-4(5H)one;

trans-rac-3-(acetyloxy)-2,3-dihydro-5-[2-(dimethylamino)ethyl]-2-(4-methoxyphenyl)naphtho[2,1-b][1,4]thiazepin-4(5H)-one;

cis-(−)-2,3-dihydro-3-hydroxy-5-[2-(dimethylamino)ethyl]-2-(4-methoxyphenyl)naphtho[2,1-b][1,4]thiazepin-4(5H)-one;

cis-(+)-2,3-dihydro-3-hydroxy-5-[2-(dimethylamino)ethyl]-2-(4-methoxyphenyl)naphtho[2,1-b][1,4]thiazepin-4(5H)-one;

cis-(−)-3-(acetyloxy)-2,3-dihydro-5-[2-(dimethylamino)ethyl]-2-(4-methoxyphenyl)naphtho[2,1-b][1,4]thiazepin-4(5H)-one;

cis-(±)-3-[(ethoxycarbonyl)oxy]-2,3-dihydro-2-(4-methoxyphenyl)-5-[2-(dimethylamino)ethyl]naphtho[2,1-b][1,4]thiazepin-4(5H)-one;

cis-(±)-2,3-dihydro-3-methoxy-5-[2-(dimethylamino)ethyl]-2-(4-methoxyphenyl)naphtho[2,1-b][1,4]thiazepin-4(5H)-one;

cis-(±)-2,3-dihydro-3-(2-methoxy-1-oxoethoxy)-2-(4-methoxyphenyl)-5-[2-(dimethylamino)ethyl]naphtho[2,1-b][1,4]thiazepin-4(5H)-one;

cis-(±)-3-[(cyclopropylcarbonyl)oxy]-2,3-dihydro-5-[2-(dimethylamino)ethyl]-2-(4-methoxyphenyl)naphtho[2,1-b][1,4]thiazepin-4(5H)-one;

cis-rac-2,3-dihydro-3-hydroxy-5-[2-(dimethylamino)ethyl]-2-(4-methoxyphenyl)naphtho[2,1-b][1,4]thiazepin-4(5H)-one;

Most preferred compounds of the formula I are:

cis-(+)-3-(acetyloxy)-2,3-dihydro-5-[2-(dimethylamino)ethyl]-2-(4-methoxyphenyl)naphtho[2,1-b][1,4]thiazepin-4(5H)-one; and cis-(+)-2,3-dihydro-3-hydroxy-5-[2-(dimethylamino)ethyl]-2-(4-methoxyphenyl)naphtho[2,1-b][1,4]thiazepin-4(5H)-one.

The compounds of formula I can be prepared as shown in Formula Scheme I below.

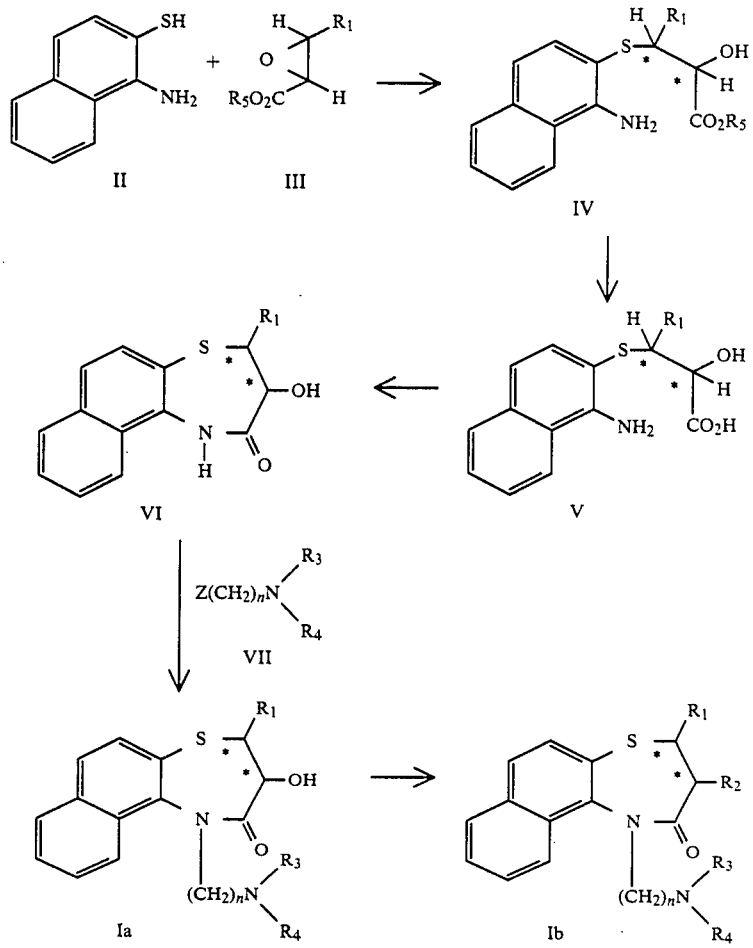

Formula Scheme I cis-rac-5-[2-(dimethylamino)propyl]-2,3-dihydro-3-hydroxy-2-(4-methoxyphenyl)naphtho[2,1-b][1,4]thiazepin-4(5H)-one;

cis-rac-3-(acetyloxy)-2,3-dihydro-2-(4-methoxyphenyl)-5-[3-(dimethylamino)propyl]naphtho[2,1-b][1,4]thiazepin-4(5H)-one;

cis-rac-5-[2-(diethylamino)ethyl]-2,3-dihydro-3-hydroxy-2-(4-methoxyphenyl)naphtho[2,1-b][1,4]thiazepin-4(5H)-one; and cis-rac-3-(acetyloxy)-5-[2-(diethylamino)ethyl]-2,3-dihydro-2-(4-methoxyphenyl)naphtho[2,1-b][1,4]thiazepin-4(5H)-one.

More preferred compounds of formula I are:

cis-rac-3-(acetyloxy)-2,3-dihydro-5-[2-(dimethylamino)ethyl]-2-(4-methoxyphenyl)naphtho[2,1-b][1,4]thiazepin-4(5H)-one; and wherein $R_1$, $R_2$, $R_3$, $R_4$ and n are as described above; Z is halogen; $R_5$ is lower alkyl and * is an asymmetric carbon.

In connection with the description below of the reactions in Formula Scheme I, the terms "SR" and "RR" refer to the relative configurations of the hydroxy and $R_1$ substituents at the 2- and 3-positions of the compounds of formula IV and V. More specifically, the term "SR" denotes compounds wherein the hydroxy and $R_1$ substituents appear on the same side of the bond between the 2- and 3-positions in a Fischer's Projection Formula. The term "RR" denotes compounds of formula IV and V wherein the hydroxy and $R_1$ substituents appear on the opposite sides of the bond between the 2- and 3-positions in a Fischer's Projection Formula. A Fischer's Projection Formula of an "SR" compound of formula V is depicted just below.

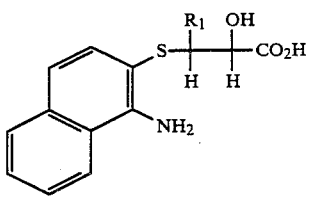

wherein R₁ is as described above.

A Fischer's Projection Formula of a "RR" compound of formula V is depicted just below

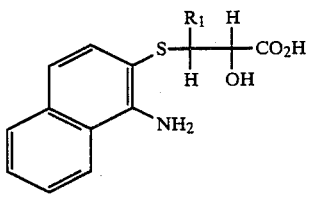

wherein $R_1$ is as described above.

In the reaction description which follows, the ester of formula IV is obtained as a mixture of "SR" and "RR" isomers which are separated by fractional crystallization.

The "SR" compounds of formulas IV and V are obtained in the form of racemates and further reacted in the form of racemates. The "RR" compounds of formulas IV and V are obtained in the form of racemates and further reacted in the form of racemates.

In connection with Formula Scheme I, 1-aminonaphthalene-2-thiol of formula II is reacted with a compound of the formula

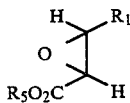

III wherein $R_1$ and $R_5$ are as described above, to give a compound of the formula

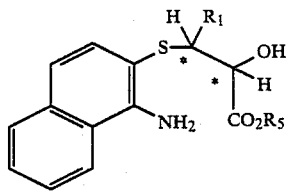

IV wherein $R_1$, $R_5$, and * are as described above.

The reaction is carried out without solvent or in the presence of an aromatic solvent such as benzene, toluene, xylene, ethylbenzene or acetonitrile in the presence of a catalytic amount of the base potassium carbonate at a temperature in the range of from about 80° to 140° for about 1 to about 20 hours under an argon or more preferably nitrogen atmosphere. The molar ratio of the reactants is not critical. Preferably, the reactants are utilized in the 1:1 molar ratio.

When the reaction is carried out in a non-polar organic solvent preferably toluene, a mixture of "SR" and "RR" compounds of formula IV result. Such a mixture can be separated by treatment with an inorganic anhydrous acid such as anhydrous hydrogen chloride in a polar organic solvent such as ethyl acetate to obtain a hydrochloride salt of an "SR" compound. The hydrochloride salt of an "SR" compound can be treated with a base such as potassium hydroxide or more preferably sodium hydroxide to obtain an "SR" compound.

When the reaction is carried out in acetonitrile in the presence of a catalytic amount of the base potassium carbonate, a "RR" compound of formula IV results. A "RR" compound of formula IV can be isolated by chromatography of the reaction mixture followed by recrystallization.

An "SR" or "RR" compound of formula IV can be hydrolyzed to the corresponding "SR" or "RR" compound of formula

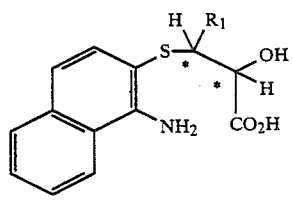

V wherein $R_1$ and * are as described above, by conventional hydrolysis methods such as, for example, treatment with an inorganic acid such as, hydrochloric or sulfuric acid, or by treatment with an alkali base such as, potassium hydroxide, or more preferably sodium hydroxide. The reaction is conducted in a polar organic solvent such as, an alkanol like propanol or more preferably ethanol at reflux for a period of about 10 minutes to about 1 hour. Separation of the product, can be by conventional means such as, crystallization.

An "SR" compound of formula V can be cyclized to the racemate of the compound of formula

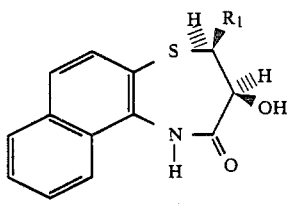

VI' wherein $R_1$ is as described above, by reaction in the presence of a catalytic amount of an acid such as p-toluenesulfonic acid in an aromatic solvent such as, benzene, xylene or more preferably toluene, at reflux for a period of about 12 to about 72 hours. Recovery of a compound of formula VI' can be by conventional means such as recrystallization.

The "RR" racemate of formula V can be cyclized to the racemate of formula

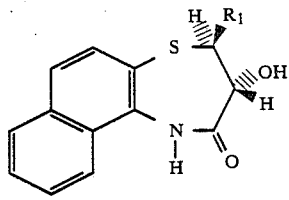

VI"

wherein $R_1$ is as described above, by heating at reflux in an aqueous inorganic acid such as aqueous sulfuric acid. Recovery of a compound of formula VI″ can be by conventional means such as recrystallization.

In the reactions described below, a compound of the formula

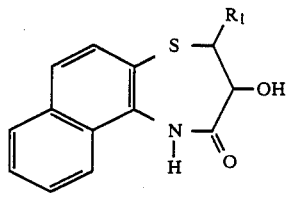

VI designates either a cis racemate of formula VI′ or a trans racemate of formula VI″.

Employing a compound of formula VI′ in the reactions described below results in a cis compound of formula I of the invention.

Employing a compound of formula VI″ in the reactions described below results in a trans compound of formula I of the invention.

A compound of formula VI can be converted to a compound of formula

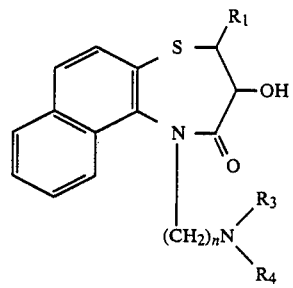

Ia wherein $R_1$, $R_3$, $R_4$ and n are as described above, by reaction with a compound of the formula

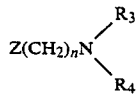

VII wherein $R_3$, $R_4$ and n are as described above, and Z is halogen, preferably chlorine.

The reaction is carried out by reacting an alkali metal salt of a compound of formula VI, such as the sodium or more preferably potassium salt thereof with an aminoalkyl halide of formula VII, preferably the chloride thereof, in a polar organic solvent such as, methyl acetate, or more preferably ethyl acetate, at about 40° to about 80°, or at the reflux temperature of the solvent employed, which in the case of ethyl acetate is 77°, for a period of about 1 hour to about 17 hours. The reaction is carried out in the presence of a base, such as, potassium hydroxide in acetone or more preferably potassium carbonate in acetone or in a lower alkyl acetate. Separation of the compound of formula Ia can be by conventional means such as, crystallization.

A compound of formula Ia, which is encompassed by compounds of formula I, can be acylated by reaction with a lower alkanoic anhydride, such as propionic anhydride, acetic anhydride, or a lower alkanoyl halide for example, acetyl, propionyl or butyryl chloride optionally in the presence of a base such as, pyridine, triethylamine, or dimethylaniline at room temperature or up to about 115°.

Alternatively, compounds of formula I wherein $R_2$ is lower alkoxy can be obtained by reacting an alkali metal salt of a compound of formula Ia such as a sodium salt (prepared by reacting a compound of formula Ia with an alkali metal hydride like sodium hydride), with an alkylating agent such as dialkyl sulfate, more particularly dimethyl sulfate in an aromatic solvent such as toluene or more preferably benzene, at about reflux temperature for a period of about 10 minutes to about 2 hours. The resulting compound of formula I can be isolated by conventional means such as crystallization.

Alternatively, a compound of formula I wherein $R_2$ is

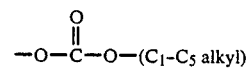

can be obtained by a reaction of a compound of formula Ia with an alkyl halo formate such as ethyl chloroformate in a basic solvent such as pyridine at about ice bath temperatures. The resulting compound of formula I can be isolated by conventional means such as crystallization.

A compound of formula I wherein $R_2$ is

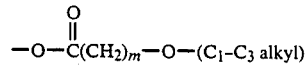

can be prepared by reacting a compound of formula Ia with an alkoxy alkanoyl halide such as, methoxyacetyl chloride in a basic solvent such as pyridine at about ice bath temperatures. The resulting compound of formula I can be isolated by conventional means such as crystallization.

A compound of formula I wherein $R_2$ is cycloalkyl carbonyloxy can be obtained by reacting a compound of formula Ia with a cycloalkylcarboxylic acid halide such as, cyclopropane carboxylic acid chloride in a basic solvent such as pyridine at about ice bath temperatures for about 1 to about 17 hours. The resulting compound of formula I can be isolated by conventional means such as extraction.

A compound of formula I wherein $R_2$ is other than hydroxy can be converted into a corresponding acid addition salt by treatment with an organic acid such as, acetic acid, oxalic acid, malonic acid, tartaric acid, malic acid, citric acid, lactic acid, maleic acid, or fumaric acid and a suitable organic solvent such as, ethyl acetate, acetone, methanol, or ethanol. Alternatively, a compound of formula I wherein $R_2$ in other than hydroxy can be converted into a corresponding acid addition salt by treatment with an inorganic acid such as sulfuric acid, hydrobromic acid, or more preferably hydrochloric acid, except in those instances where the $R_2$ substituent would be cleaved by such treatment. The resulting compound of formula I where $R_2$ is hydroxy can be converted into the corresponding acid addition salt by treatment with an organic acid as described above or an inorganic acid such as, hydrochloric acid, in a suitable organic solvent such as ethyl acetate.

Alternatively, prior to the above described conversion of a compound formula Ia to the other compounds of formula I, and the salt forming steps, a cis compound of formula Ia which is produced as a racemate can be resolved into its optically active enantiomers. The solution of a particular cis compound of formula Ia', that is, cis-rac-2,3-dihydro-3-hydroxy-5-[2-(dimethylamino)ethyl]-2-(4-methoxyphenyl)naphtho[2,1-b][1,4]thiazepin-4(5H)-one is shown in Formula Scheme II. The resolution of other compounds of formula Ia may require, for example, other conventional resolving agents.

Formula Scheme II

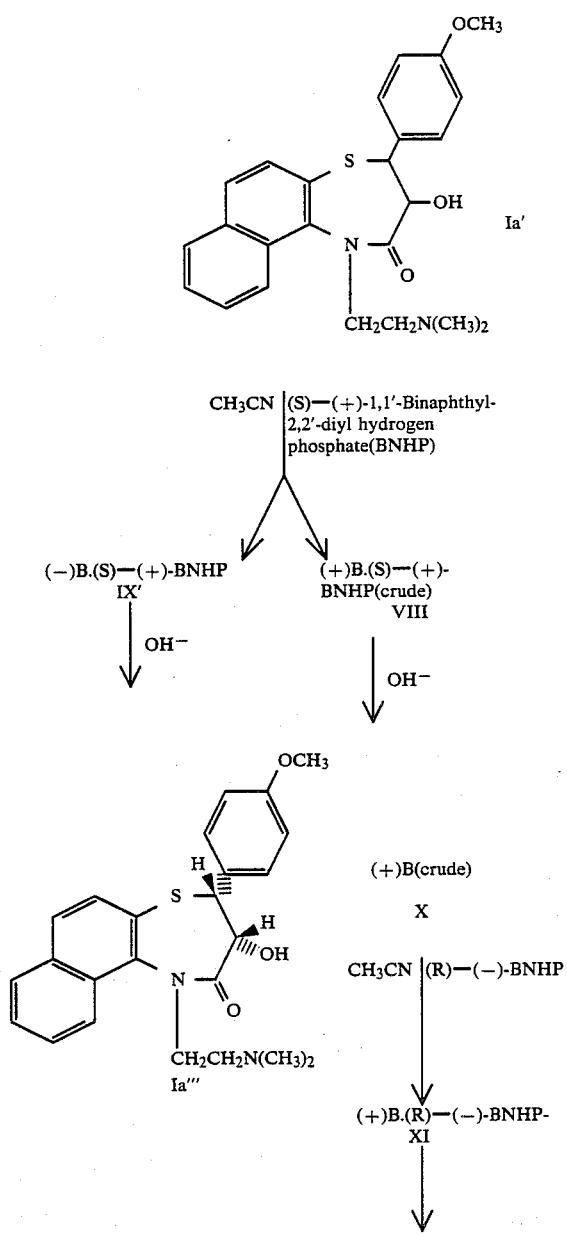

-continued
Formula Scheme II

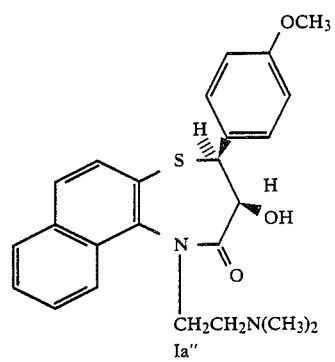

Ia"

wherein (+)B and (−)B are respectively the (+)- and (−)-enantiomers of the compound of formula Ia', cis-rac-2,3-dihydro-3-hydroxy-5-[2-(dimethylamino)ethyl]-2-(4-methoxyphenyl)naphtho[2,1-b][1,4]thiazepin-4(5H)-one.

In connection with Formula Scheme II above, a racemate of the formula Ia' in a polar, aprotic organic solvent such as, acetonitrile, is treated with a hot acetonitrile solution of a resolving agent such as s-(+)-1,1'-binaphthyl-2,2'-diyl hydrogen phosphate abbreviated as BNHP and the resulting solution is allowed to crystallize at about room temperature. The crystals are a salt of formula IX' of the resolving agent and the (−)-enantiomer of the compound of formula Ia'. The soluble salt is that of the (+)-enantiomer of the compound of formula Ia' and the resolving agent. This is the solution of formula VIII in Formula Scheme II above.

The crystals of the salt of formula IX' are collected by filtration.

The salt of formula IX' can be treated in water with a base such as sodium hydroxide or more preferably concentrated ammonium hydroxide then the aqueous suspension extracted with an organic solvent such as methylene chloride and concentrated to obtain the (−)-enantiomer of formula Ia'''. This (−)-enantiomer can be used in the above described reactions of compounds of formula Ia.

The above solution of formula VIII is concentrated and treated in water with a base such as sodium hydroxide or more preferably concentrated ammonium hydroxide and extracted with an organic solvent such as ether and concentrated to give the crude (+)-enantiomer of formula X of the Formula Scheme II. The crude (+)-enantiomer of formula X can be further purified by dissolving in hot acetonitrile, and treating the resulting solution with a resolving agent such as R(−)-1,1'-binaphthyl-2,2'-diyl hydrogen phosphate in acetonitrile. A salt of this resolving agent and the (+)-enantiomer of formula XI results. The just above mentioned salt can be suspended in water and treated with a base such as, concentrated ammonium hydroxide, and the resulting suspension can be extracted with organic solvents such as, ether. The (+)-enantiomer of formula Ia" can be isolated from the solution by evaporation of the solvent and can be used in the above described reactions for compounds of formula Ia.

The trans racemates of formula Ia can be similarly resolved by using other conventional resolving agents.

The compound of formula II, that is, 1-amino-naphthalene-2-thiol, can be prepared as follows. To a solution of a base such as potassium hydroxide or more preferably sodium hydroxide and an alkylene glycol such as ethylene glycol, is added naphtho[1,2-d]thiazol-2-amine which is a known compound or can be prepared according to known methods. The mixture is heated at reflux under an inert atmosphere such as nitrogen for about 10 to about 25 hours, diluted with water then neutralized with acetic acid. The aqueous suspension is extracted with ether and the solvent is removed. The compound of formula II, that is, 1-amino-naphthalene-2-thiol, is obtained from the residue by conventional means.

The compounds of formula III, are known compounds or can be prepared according to known methods. Exemplary of compounds of formula III are:
trans-3-(p-methoxyphenyl)glycidate; and
trans-3-(p-ethoxyphenyl)glycidate.

The compounds of formula VII are known compounds or can be prepared according to known methods. Exemplary of the compounds of formula VII are:
2-dimethylaminoethyl chloride;
2-dimethylaminoethyl bromide;
2-diethylaminoethyl chloride;
2-dipropylaminoethyl chloride; and
3-dimethylaminopropyl chloride.

The compounds of formula I, including the pharmaceutically acceptable acid addition salts thereof, are calcium antagonists, more specifically, calcium channel blockers, and therefore useful as agents in lowering blood pressure and in treating ischemia. Their pharmocologically useful activities are demonstrated in warm-blooded animals using standard procedures which are set forth below.

GUINEA PIG ILEUM ASSAY—TONIC CONTRACTION

Male guinea-pigs weighing from 300-400 grams were stunned and bled. The abdomen was opened and 10-15 cm of terminal ileum was carefully removed and cleaned and placed in Tyrode's Solution of the following composition: NaCl (8 g/l), KCl (0.2 g/l), $MgCl_2$ (0.2 g/l.), $CaCl_2$ (0.2 g/l), $NaH_2PO_4$ (0.05 g/l), $NaHCO_3$ (1.0 g/l) and Glucose (1 g/l). The solution was maintained at 37° C. and gassed with 95% $O_2$ and 5% $CO_2$. Portions of the ileum were placed over a glass rod, a shallow incision was made the length of the mesenteric attachment just severing the outer-longitudinal muscle layer. The longitudinal muscle was separated from the underlying circular muscle by gentle dissection (Rang, H. P. Annals of N.Y. Academy of Science Vol. 144, page 756, (1964)). The tissue was fixed at one end to a tissue holder, the other end was connected by a thread to a force transducer and suspended in a muscle bath containing Tyrode's Solution maintained at 37° C. and gassed with 95% $O_2$ and 5% $CO_2$. An initial tension of 500 mg was applied and the tissue allowed to equilibrate for 60 minutes prior to the start of the study. During this period the tissue was washed every 16 minutes. Each preparation, at 16 minute intervals, was challenged with KCl sufficient to yield a bath $K^+$ concentration of 80 mMK for 2 minutes, then washed with fresh solution. The 16 minute interval between $K^+$ challenges was maintained throughout the study. Upon stabilization of the responses to the $K^+$ challenge the test compound (potential calcium entry antagonist) was introduced into the bath 2 minutes prior to and during the 2 minute exposure to $K^+$ after which the bath was cleared and washed with fresh solution. Logarithmically increasing doses (up to $10^{-4}$M) of the potential antagonist were administered as the study progressed.

The measure of compound's ability to inhibit the tonic contraction of muscle is a measure of its activity as a calcium channel blocking agent. The $IC_{50}$ is that concentration at which a compound inhibits the tonic contraction of muscle by 50%.

The activity of compounds of the invention in this test is given in the Table I which follows.

TABLE 1

| Compounds | Guinea Pig Ileum Tonic $IC_{50}$ ($\mu M$) |
|---|---|
| A | $4.0 \times 10^{-7}$ |
| B | $4.5 \times 10^{-7}$ |
| C | $2.3 \times 10^{-7}$ |
| D | $3.9 \times 10^{-7}$ |
| E | $2.5 \times 10^{-7}$ |

In the above Table, compound A is cis-rac-2,3-dihydro-3-hydroxy-5-[2-(dimethylamino)ethyl]-2-(4-methoxyphenyl)naphtho[2,1-b][1,4]thiazepin-4(5H)-one hydrochloride;

compound B is cis-rac-3-(acetyloxy)-2,3-dihydro-5-[2-(dimethylamino)ethyl]-2-(4-methoxyphenyl)naphtho[2,1-b][1,4]thiazepin-4(5H)-one (E)-2-butendioate;

compound C is cis-(+)-2,3-dihydro-3-hydroxy-5-[2-(dimethylamino)ethyl]-2-(4-methoxyphenyl)naphtho[2,1-b][1,4]thiazepin-4(5H)-one hydrochloride semihydrate;

compound D is cis-(+)-3-(acetyloxy)-2,3-dihydro-5-[2-(dimethylamino)ethyl]-2-(4-methoxyphenyl)naphtho[2,1-b][1,4]thiazepin-4(5H)-one (E)-2-butendioate; and compound E is diltiazem hydrochloride.

The compounds of formula I, and the pharmaceutically acceptable acid addition salts thereof, as herein described, can be incorporated into standard pharmaceutical dosage forms. The compounds of formula I are useful for oral or parenteral application with the usual pharmaceutical carrier materials, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, or capsules, or in liquid form, for example as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The invention also relates to a method of inducing calcium antagonist activity in a warm-blooded animal in need of such treatment which comprises administering an effective amount of a compound of formula I. The invention also relates to a method of lowering blood pressure or treating ischemia by bringing about myocardial preservation during ischemia, which comprises administering an effective amount of a compound of formula I, or pharmaceutically acceptable acid addition salts thereof to a warm-blooded animal in need of such treatment. The amount of an oral daily dosage can be determined by one skilled in the art and would be comparable to that of diltiazem. The amount of an intravenous dosage can also be determined by one skilled in the art and is comparable to that of diltiazem. It is to be understood, however, that dosages may vary from individual to individual and accordingly the above recitation is not intended to limit the scope of the present invention in any way.

The following examples further illustrate the invention. All temperatures are in degrees Celsius, unless otherwise mentioned.

EXAMPLE 1

Naphtho[1,2-d]thiazol-2-amine

To 160 ml thionyl chloride 64.0 g (0.32 mol) of 1-(1-naphthyl)-2-thiourea was added portionwise while the temperature of the reaction mixture was kept at 30°–40° (internal temperature). After the addition was completed, an additional 80 ml of thionyl chloride was added and the mixture was heated at 50°–55° for 4 hours. It was cooled to room temperature and diluted with 400 ml of ethyl acetate and filtered. The filtrate in 400 ml of water was basified with concentrated ammonium hydroxide and the aqueous suspension was extracted with ethyl acetate (3×200 ml). The combined ethyl acetate solutions were dried (MgSO$_4$) and the solvent was removed under reduced pressure to give 46.6 g (74%) of naphtho[1,2-d]thiazol-2-amine, mp 186°–188°.

EXAMPLE 2

1-Aminonaphthalene-2-thiol

To a solution of 30.0 g sodium hydroxide in 30 ml of water and 180 ml of ethylene glycol was added 18.0 g (0.089 mol) of naphtho[1,2-d]thiazol-2-amine. The mixture was stirred and heated at reflux under nitrogen for 20 hours then diluted with 100 ml of water. After cooling to room temperature the mixture was extracted with ether (4×95 ml). The aqueous solution was cooled in an ice-bath and neutralized with acetic acid. The aqueous suspension was extracted with ether (3×175 ml). The combined ether solutions were washed with water and dried (MgSO$_4$). Removal of the solvent gave a residue to which heptane (3×50 ml) was added and distilled off under reduced pressure to give 10.5 g (67%) of 1-aminonaphthalene-2-thiol. This compound is sensitive to air, and therefore was used immediately for the condensation with the glycidate. For analysis a sample of this compound was distilled at 110°–115° (0.05 mm), mp 36°–37°.

C$_{10}$H$_9$NS(175.18). Calcd: C, 68.56; H, 5.18; N, 8.00. Found: C, 68.78; H, 5.12; N, 7.96.

EXAMPLE 3

(±)-(S*,R*)- and (R*,R*)-β-[(1-Amino-2-naphthalenyl)thio]-α-hydroxy-4-methoxybenzenepropanoic Acid Methyl Ester Under nitrogen a mixture of 8.5 g (0.048 mol) of 1-aminonaphthalene-2-thiol and 10.1 g (0.048 mol) of trans-3-(p-methoxyphenyl)glycidate in 150 ml toluene was heated at 120° for 2 hours. The mixture was concentrated to a lower volume, the crystals were filtered then washed with ether and dried to afford 8.75 g (47%) of pure (±)-(S*,R*)-β-[(1-amino-2-naphthalenyl)thio]-α-hydroxy-4-methoxybenzenepropanoic acid methyl ester, mp 132°–134°.

Gas chromatographic analysis of the crude product indicated a 24:1 ratio of (S*,R*): (R*,R*) ester.

C$_{21}$H$_{21}$NO$_4$S(383.46). Calcd: C, 65.78; H, 5.52; N, 3.65. Found: C, 65.46; H, 5.49; N, 3.65.

EXAMPLE 4

A sample of the above (S*,R*) base, on treatment with hydrogen chloride (anhydrous) in acetonitrile afforded the crude hydrochloride, which after recrystallization from methanol-ether gave (±)-(S*,R*)-β-[(1-amino-2-naphthalenyl)thio]-α-hydroxy-4-methoxybenzenepropanoic acid methyl ester hydrochloride, mp 166°–168°.

C$_{21}$H$_{21}$NO$_4$S.HCl(419.92). Calcd: C, 60.07; H, 5.28; N, 3.34. Found: C, 59.96; H, 5.45; N, 3.48.

EXAMPLE 5

Base Catalyzed Reaction of 1-Aminonaphthalene-2-thiol with trans-3-(p-Methoxyphenyl)glycidate Under nitrogen, a mixture of 4.1 g (0.023 mol) of 1-aminonaphthalene-2-thiol and 5.0 g (0.024 mol) of trans-3-(p-methoxyphenyl)glycidate and 0.5 g of potassium carbonate in 80 ml acetonitrile was stirred at reflux for 2 hours. After cooling to room temperature the mixture was filtered and the filtrate was concentrated to dryness to give 8.7 g of a mixture of rac-(R*,R*)-β-[(1-amino-2-naphthalenyl)thio]-α-hydroxy-4-methoxybenzenepropanoic acid methyl ester, 1H-naphtho[2,1-b][1,4]thiazin-2(3H)-one, and p-methoxybenzaldehyde. The mixture was dissolved in methylene chloride and chromatographed on a column using 120 g of silica gel. The column was eluted with 75 ml portions of methylene chloride. Fractions 3–9 which were collected, and the solvent which was removed under reduced pressure afforded 0.6 g of an oil whose NMR spectrum was identical with that of p-methoxybenzaldehyde. Fractions 13–18 gave 1.40 g (28%) of 1H-naphtho[2,1-b][1,4]thiazin-2(3H)-one. For analysis a sample of this compound was crystallized from acetone, mp 195°–196°.

C$_{12}$H$_9$NOS (215.27). Calcd: C, 66.95; H, 4.21; N, 6.51. Found: C, 66.97; H, 4.24; N, 6.48.

Further elution of the column with the same solvent (fractions 25–40) afforded 1.0 g (11%) of racemic (R*,R*)-β-[(1-amino-2-naphthalenyl)thio]-α-hydroxy-4-methoxybenzenepropanoic acid methyl ester, mp 125°–126°. The analyzed sample was recrystallized from ether, mp 125°–126°.

C$_{21}$H$_{21}$NO$_4$S (383.46). Calcd: C, 65.78; H, 5.52; N, 3.65. Found: C, 65.65; H, 5.58; N, 3.94.

EXAMPLE 6

(±)-(S*,R*)-β-[(1-Amino-2-naphthalenyl)thio]-α-hydroxy-4-methoxybenzenepropanoic Acid A mixture of 8.9 g (0.023 mol) of (±)-(S*,R*)-β-[(1-amino-2-naphthalenyl)thio]-α-hydroxy-4-methoxybenzenepropanoic acid methyl ester, 50 ml ethanol and 140 ml 1N sodium hydroxide was heated at reflux for 30 minutes. The reaction mixture was cooled to room temperature, diluted with water (50 ml) and extracted with ether (2×75 ml). The aqueous solution was chilled, then neutralized with acetic acid and extracted with ethyl acetate (3×75 ml). The combined extracts were washed with water (75 ml) and dried (MgSO$_4$). Removal of the solvent gave 8.2 g (96%) of (±)-(S*,R*)-β-[(1-amino-2-naphthalenyl)thio]-α-hydroxy-4-methoxybenzenepropanoic acid, mp 167°–168°. The analyzed sample was recrystallized from ethyl acetate, mp 167°–168°.

C$_{20}$H$_{19}$NO$_4$S (369.43). Calcd: C, 65.02; H, 5.18; N, 3.79. Found: C, 64.88; H, 5.10; N, 3.77.

EXAMPLE 7

(±)-(R*,R*)-β-[(1-Amino-2-naphthalenyl)thio]-α-hydroxy-4-methoxybenzenepropanoic acid A mixture of 6.6 g (0.017 mol) of (±)-(R*,R*)-β-[(1-amino-2-naphthalenyl)thio]-α-hydroxy-4-methoxybenzenepropanoic acid methyl ester, 45 ml ethanol and 100 ml 1N sodium hydroxide was heated at reflux for 30 minutes. The reaction mixture was cooled to room temperature, diluted with water (50 ml) and extracted with ether. The aqueous solution was chilled, then neutralized with acetic acid and extracted with ethyl acetate (3×60 ml). The combined extracts were washed with water (50 ml) and dried (MgSO$_4$). Removal of the solvent gave 5.5 g of crude (±)-(R*,R*)-β-[(1-amino-2-naphthalenyl)thio]-α-hydroxy-4-methoxybenzenepropanoic acid which was dissolved in methylene chloride and chromatographed on a column using 55 g of silica gel. The column was eluted with 50 ml portions of methylene chloride. Fractions 12–17 were collected, and the solvent was removed under reduced pressure to afford 1.3 g (20%) of (±)-(R*,R*)-β-[(1-amino-2-naphthalenyl)thio]-α-hydroxy-4-methoxybenzenepropanoic acid. The analyzed sample was recrystallized from ether, mp 160°–161°.

$C_{20}H_{19}NO_4S$ (369.43). Calcd: C, 65.02; H, 5.18; N, 3.79. Found: C, 64.83; H, 5.52; N, 3.81.

EXAMPLE 8

Cyclization of (±)-(R*,R*)-β-[(1-Amino-2-naphthalenyl)thio]-α-hydroxy-4-methoxybenzenepropanoic Acid (±)-(R*,R*)-β-[(1-Amino-2-naphthalenyl)thio]-α-hydroxy-4-methoxybenzenepropanoic acid, 1.0 g (0.003 mol) was dissolved in acetone and acidified with hydrogen chloride. (EtOAc—HCl). The solvent was removed under reduced pressure and the residue in 100 ml 20% sulfuric acid was heated at reflux for 2 hours. The mixture was cooled to room temperature and the (±)-trans-2,3-dihydro-3-hydroxy-2-(4-methoxyphenyl)naphtho[2,1-b][1,4]thiazepin-4(5H)-one was separated by filtration to give 0.69 (66%) of the just above named compound. The analyzed sample was recrystallized from acetonitrile, mp 300°–301°.

$C_{20}H_{17}NO_3S$ (351.42). Calcd: C, 68.36; H, 4.88; N, 3.99. Found: C, 68.21; H, 4.99; N, 4.51.

EXAMPLE 9

(±)-cis-2,3-Dihydro-3-hydroxy-2-(4-methoxyphenyl)-naphtho[2,1-b][1,4]thiazepin-4(5H)-one A mixture of 2.0 g (0.0054 mol) of (±)-(S*,R*)-β-[(1-amino-2-naphthalenyl)thio]-α-hydroxy-4-methoxybenzenepropanoic acid and a few crystals of p-toluenesulfonic acid in 150 ml toluene was heated at reflux for 17 hours. Most of the solvent was removed under reduced pressure and the crystals were separated by filtration to give 1.5 g (79%) of (±)-cis-2,3-dihydro-3-hydroxy-2-(4-methoxyphenyl)naphtho[2.1-b][1,4]thiazepin-4(5H)-one, mp 255°–256°. The analyzed sample was recrystallized from methylene chloride methanol, mp 255°–256°.

$C_{20}H_{17}NO_3S$ (351.42). Calcd: C, 68.36; H, 4.88; N, 3.99. Found: C, 68.15; H, 4.89; N, 3.75.

EXAMPLE 10

(±)-cis-2,3-Dihydro-3-hydroxy-5-[2-(dimethylamino)ethyl]-2-(4-methoxyphenyl)naphtho[2,1-b][1,4]thiazepin-4(5H)-one A mixture of 4.4 g (0.013 mol) of (±)-cis-2,3-dihydro-3-hydroxy-2-(4-methoxyphenyl)naphtho[2,1-b][1,4]thiazepin-4(5H)-one, 2.0 g of powdered potassium carbonate and 1.6 g (0.132 mol) of 2-dimethylaminoethyl chloride in 100 ml ethyl acetate was stirred and heated at reflux for 2 hours then three times an additional 0.4 g of 2-dimethylaminoethyl chloride was added at 2 hour intervals. The mixture was heated at reflux for a total of 12 hours, then was cooled to room temperature and filtered. The filtrate was diluted with ethyl acetate (150 ml) and washed with water (100 ml). The ethyl acetate solution was dried (MgSO$_4$) and removal of the solvent gave 3.6 g (68%) of (±)-cis-2,3-dihydro-3-hydroxy-5-[2-(dimethylamino)ethyl]-2-(4-methoxyphenyl)naphtho[2,1-b][1,4]thiazepin-4(5H)-one, mp 128°–130°.

$C_{24}H_{26}N_2O_3S$ (422.54). Calcd: C, 68.22; H, 6.20; N, 6.63. Found: C, 68.17; H, 6.29; N, 6.44.

EXAMPLE 11

(±)-cis-2,3-Dihydro-3-hydroxy-5-[2-(dimethylamino)ethyl]-2-(4-methoxyphenyl)naphtho[2,1-b][1,4]thiazepin-4(5H)-one Hydrochloride A sample of the product of Example 10, on treatment with hydrogen chloride (anhydrous) in acetone afforded the hydrochloride, which after recrystallization from methyl ethyl ketone gave (±)-cis-2,3-dihydro-3-hydroxy-5-[2-(dimethylamino)ethyl]-2-(4-methoxyphenyl)naphtho[2,1-b][1,4]thiazepin-4(5H)-one hydrochloride, mp 155°–156°.

$C_{24}H_{26}N_2O_3S \cdot HCl$ (459.00). Calcd: C, 62.80; H, 5.93; N, 6.10. Found: C, 62.95; H, 6.28; N, 5.69.

EXAMPLE 12

(±)-cis-3-(Acetyloxy)-2,3-dihydro-5-[2-(dimethylamino)ethyl]-2-(4-methoxyphenyl)naphtho[2,1-b][1,4]thiazepin-4(5H)-one A mixture of 1.5 g (0.0035 mol) of (±)-cis-2,3-dihydro-3-hydroxy-5-[2-(dimethylamino)ethyl]-2-(4-methoxyphenyl)naphtho[2,1-b][1,4]thiazepin-4(5H)-one and 25 ml of acetic anhydride was heated at 100° for 17 hours. The excess of reagent was removed under reduced pressure and the residue was partitioned between dilute ammonium hydroxide and ethyl acetate. The ethyl acetate solution was washed with water (50 ml) and dried (MgSO$_4$). Removal of the solvent gave 1.2 g (73%) of (±)-cis-3-(acetyloxy)-2,3-dihydro-5-[2-(dimethylamino)ethyl]-2-(4-methoxyphenyl)naphtho[2,1-b][1,4]thiazepin-4(5H)-one. For analysis, a sample of this compound was recrystallized from ether, mp 168°–169°.

$C_{16}H_{28}N_2O_4S$ (464.58). Calcd: C, 67.22; H, 6.07; N, 6.03. Found: C, 67.06; H, 6.27; N, 5.97.

EXAMPLE 13

(±)-cis-3-(Acetyloxy)-2,3-dihydro-5-[2-(dimethylamino)ethyl]-2-(4-methoxyphenyl)naphtho[2,1-b][1,4]thiazepin-4(5H)-one (E)-2-Butenedioate 1.9 g (0.004 mol) of the product of Example 12, on treatment with 0.47 g (0.004 mol) of fumaric acid in 50 ml acetone gave 2.0 g (87%) of (±)-cis-3-(acetyloxy)-

2,3-dihydro-5-[2-(dimethylamino)ethyl]-2-(4-methoxyphenyl)naphtho[2,1-b][1,4]thiazepin-4(5H)-one (E)-2-butenedioate. The analyzed sample was recrystallized from ethanol, mp 221°–222°.

$C_{26}H_{28}N_2O_4S \cdot C_4H_4O_4$ (580.65). Calcd: C, 62.06; H, 5.55; N, 4.82. Found: C, 62.26; H, 5.71; N, 4.85.

EXAMPLE 14

(±)-trans-2,3-Dihydro-3-hydroxy-5-[2-(dimethylamino)ethyl]-2-(4-methoxyphenyl)naphtho[2,1-b][1,4]thiazepin-4(5H)-one A mixture of 2.4 g (0.0068 mol) of (±)-trans-2,3-dihydro-3-hydroxy-2-(4-methoxyphenyl)naphtho[2,1-b][1,4]thiazepin-4(5H)-one, 1.0 g of potassium carbonate (powdered) and 0.8 g (0.0068 mol) of 2-dimethylaminoethyl chloride in 60 ml ethyl acetate was stirred and heated at reflux for 2 hours, then three times an additional 0.2 g of 2-dimethylaminoethyl chloride was added at 2 hour intervals. The mixture was heated at reflux for a total of 12 hours, then was cooled to room temperature and filtered. The filtrate was diluted with ethyl acetate (150 ml) and washed with water. The ethyl acetate solution was dried (MgSO$_4$) and removal of the solvent gave 1.9 g (66%) of (±)-trans-2,3-dihydro-3-hydroxy-5-[2-(dimethylamino)ethyl]-2-(4-methoxyphenyl)naphtho[2,1-b][1,4]thiazepin-4(5H)-one, mp 155°–156°. The analyzed sample was recrystallized from acetone, mp 155°–156°.

$C_{24}H_{26}N_2O_3S$ (422.54). Calcd: C, 68.22; H, 6.20; N, 6.63. Found: C, 68.44; H, 6.28; N, 6.59.

EXAMPLE 15

(±)-trans-2,3-Dihydro-3-hydroxy-5-[2-(dimethylamino)ethyl]-2-(4-methoxyphenyl)naphtho[2,1-b][1,4]thiazepin-4(5H)-one Hydrochloride Semihydrate A sample of the product of Example 14, on treatment with hydrogen chloride (anhydrous) in acetone afforded (±)-trans-2,3-dihydro-3-hydroxy-5-[2-(dimethylamino)ethyl]-2-(4-methoxyphenyl)naphtho[2,1-b][1,4]thiazepin-4(5H)-one hydrochloride semihydrate, mp 193°–194°. The analyzed sample was recrystallized from acetone, mp 193°–194°.

$C_{24}H_{26}N_2O_3S \cdot HCl \cdot 0.5H_2O$ (468.01). Calcd: C, 61.59; H, 6.03; N, 5.99. Found: C, 61.74; H, 6.01; N, 5.88.

EXAMPLE 16

(±)-trans-3-(Acetyloxy)-2,3-dihydro-5-[2-(dimethylamino)ethyl]-2-(4-methoxyphenyl)naphtho[2,1-b][1,4]thiazepin-4(5H)-one To a solution of 1.0 g (0.0024 mol) of (±)-trans-2,3-dihydro-3-hydroxy-5-[2-(dimethylamino)ethyl]-2-(4-methoxyphenyl)naphtho[2,1-b][1,4]thiazepin-4(5H)-one in 20 ml of pyridine was added dropwise 0.5 g (0.006 mol) of acetyl chloride at ice-bath temperature. The mixture was stirred at ice-bath temperature for 17 hours and concentrated to dryness. The residue was partitioned between dilute ammonium hydroxide and ethyl acetate. The ethyl acetate solutions were washed with water (50 ml) and dried (MgSO$_4$). Removal of the solvent gave 1.0 g (92%) of (±)-trans-3-(acetyloxy)-2,3-dihydro-5-[2-(dimethylamino)ethyl]-2-(4-methoxyphenyl)naphtho[2,1-b][1,4]thiazepin-4(5H)-one. The analyzed sample was recrystallized from ether, mp 170°–171°.

$C_{26}H_{28}N_2O_4S$ (464.58). Calcd: C, 67.22; H, 6.07; N, 6.03. Found: C, 67.23; H, 6.27; N, 6.04.

EXAMPLE 17

(±)-trans-3-(Acetyloxy)-2,3-dihydro-5-[2-(dimethylamino)ethyl]-2-(4-methoxyphenyl)naphtho[2,1-b][1,4]thiazepin-4(5H)-one (E)-2-Butenedioate Monohydrate 0.5 g (0.0001 mol) of the product of Example 16 on treatment with 0.12 g (0.0001 mol) of fumaric acid in acetone gave 0.6 g (93%) of (±)-trans-3-(acetyloxy)-2,3-dihydro-5-[2-(dimethylamino)ethyl]-2-(4-methoxyphenyl)naphtho[2,1-b][1,4]thiazepin-4(5H)-one (E)-2-butenedioate monohydrate, mp 155°–156°.

$C_{26}H_{28}N_2O_4S \cdot C_4H_4O_4 \cdot H_2O$ (598.68). Calcd: C, 60.19; H, 5.72; N, 4.68. Found: C, 60.09; H, 5.55; N, 4.40.

EXAMPLE 18

Resolution of (±)-cis-2,3-Dihydro-3-hydroxy-5-[2-(dimethylamino)ethyl]-2-(4-methoxyphenyl)naphtho[2,1-b][1,4]thiazepin-4(5H)-one A hot solution of 17.7 g (0.042 mol) of racemic cis-2,3-dihydro-3-hydroxy-5-[2-(dimethylamino)ethyl]-2-(4-methoxyphenyl)naphtho[2,1-b][1,4]thiazepin-4(5H)-one in 177 ml of acetonitrile was combined with a hot solution of 14.59 g (0.042 mol) of S-(+)-1,1'-binaphthyl-2,2'-diyl hydrogen phosphate in 730 ml of acetonitrile. The clear solution was allowed to crystallize at room temperature for 17 hours. The crystals were then collected by filtration, washed with acetonitrile and dried, affording 11.7 g (72%) of (−)-cis-2,3-dihydro-3-hydroxy-5-[2-(dimethylamino)ethyl]-2-(4-methoxyphenyl)naphtho[2,1-b][1,4]thiazepin-4(5H)-one S-4-hydroxydinaphtho[2,1:1,2'-f][1,3,2]dioxaphosphepin-4-oxide, mp 179°–181°, $[\alpha]_D^{25} +145.96°$ (C 0.48, MeOH).

$C_{24}H_{26}N_2O_3S \cdot C_{20}H_{13}O_4P$ (770.76). Calcd: C, 68.56; H, 5.10; N, 3.63. Found: C, 60.40; H, 5.27; N, 3.60.

EXAMPLE 19

(−)-cis-2,3-Dihydro-3-hydroxy-5-[2-(dimethylamino)ethyl]-2-(4-methoxyphenyl)naphtho[2,1-b][1,4]thiazepin-4(5H)-one (−)-cis-2,3-Dihydro-3-hydroxy-5-[2-(dimethylamino)ethyl]-2-(4-methoxyphenyl)naphtho[2,1-b][1,4]thiazepin-4(5H)-one S-4-hydroxydinaphtho[2,1-d:1',2'-f][1,3,2]dioxaphosphepin-4-oxide, 11.7 g (0.015 mol) in 200 ml of water was decomposed with concentrated ammonium hydroxide. The resulting suspension was extracted with ether (3×250 ml). The combined ether solutions were washed with water (75 ml) and dried (MgSO$_4$). Removal of the solvent gave 6.4 g (100%) of (−)-cis-2,3-dihydro-3-hydroxy-5-[2-(dimethylamino)ethyl]-2-(4-methoxyphenyl)naphtho[2,1-b][1,4]thiazepin-4(5H)-one. The analyzed sample was crystallized from ether, mp 40°–41°, $[\alpha]_D^{25} -183.31°$ (C 0.91, MeOH). A 100 MHz NMR spectrum of the title compound in CHCl$_3$ in the presence of chiral shift reagent Eu(TFC)$_3$ indicated that the sample is enantiomerically pure.

$C_{24}H_{26}N_2O_3S$ (422.54). Calcd: C, 68.23; H, 6.20; N, 6.63. Found: C, 68.36; H, 6.26; N, 6.59.

EXAMPLE 20

(−)-cis-2,3-Dihydro-3-hydroxy-5-[2-(dimethylamino)ethyl]-2-(4-methoxyphenyl)naphtho[2,1-b][1,4]thiazepin-4(5H)-one Monohydrochloride Semihydrate A sample of the product of Example 19, on treatment with hydrogen chloride (anhydrous) in ethyl acetate gave amorphous (−)-cis-2,3-dihydro-3-hydroxy-5-[2-(dimethylamino)ethyl]-2-(4-methoxyphenyl)naphtho[2,1-b][1,4]thiazepin-4(5H)-one monohydrochloride semihydrate, $[\alpha]_D^{25} -170.02°$ (C 0.95, MeOH).

$C_{24}H_{26}N_2O_3S \cdot HCl \cdot 0.5H_2O$ (468.01). Calcd: C, 61.59; H, 6.03; N, 5.99. Found: C, 61.88; H, 6.10; N, 5.96.

EXAMPLE 21

(+)-cis-2,3-Dihydro-3-hydroxy-5-[2-(dimethylamino)ethyl]-2-(4-methoxyphenyl)naphtho[2,1-b][1,4]thiazepin-4(5H)-one R-(−)-BNHP The combined mother liquors obtained in the preparation of (−)-base S(+)-1,1'-binaphthyl-2,2'-diyl hydrogen phosphate were concentrated to dryness. The residue is 200 ml water was decomposed with concentrated ammonium hydroxide, and the resulting suspension was extracted with ether (3×350 ml). The combined extracts were washed with water (100 ml) and dried (MgSO$_4$). Removal of the solvent gave 10.60 g of crude (+)-cis-2,3-dihydro-3-hydroxy-5-[2-(dimethylamino)ethyl]-2-(4-methoxyphenyl)naphtho[2,1-b][1,4]thiazepin-4(5H)-one. Of this compound 10.6 g (0.025 mol) were dissolved in 100 ml hot acetonitrile and combined with a hot solution of 8.68 g (0.025 mol) of R(−)-1,1'-binaphthyl-2,2'-diyl hydrogen phosphate in 400 ml of acetonitrile. The solution was allowed to crystallize at room temperature for 17 hours. The crystals were collected by filtration, washed with acetonitrile and dried, thus affording 13.4 g (83%) of (+)-cis-2,3-dihydro-3-hydroxy-5-[2-(dimethyamino)ethyl]-2-(4-methoxyphenyl)naphtho[2,1-b][1,4]thiazepin-4(5H)-one (R)-4-hydroxydinaphtho[2,1-d:1',2'-f][1,3,2]dioxaphosphepin-4-oxide, mp 277°–279°, $[\alpha]_D^{25} -145.96°$ (C 1.03, MeOH).

$C_{24}H_{26}N_2O_3S \cdot C_{20}H_{13}O_4P$ (770.76). Calcd: C, 68.56; H, 5.10; N, 3.63. Found: C, 68.28; H, 5.06; N, 3.73.

EXAMPLE 22

(+)-cis-2,3-Dihydro-3-hydroxy-5-[2-(dimethylamino)ethyl]-2-(4-methoxyphenyl)naphtho[2,1-b][1,4]thiazepin-4(5H)-one (+)-cis-2,3-Dihydro-3-hydroxy-5-[2-(dimethylamino)ethyl]-2-(4-methoxyphenyl)naphtho[2,1-b][1,4]thiazepin-4(5H)-one (R)-4-hydroxydinaphtho[2,1-d:1',2'-f][1,3,2]dioxaphosphepin-4-oxide, 13.5 g (0.018 mol) in water (200 ml) was decomposed with concentrated ammonium hydroxide. The resulting suspension was extracted with ether (3×250 ml). The combined ether solutions were washed with water (75 ml) and dried (MgSO$_4$). Removal of the solvent gave 7.4 g (100%) of (+)-cis-2,3-dihydro-3-hydroxy-5-[2-(dimethylamino)ethyl]-2-(4-methoxyphenyl)naphtho[2,1-b][1,4]thiazepin-4(5H)-one. The analytical sample was crystallized from ether-pet. ether mp 40°–41°, $[\alpha]_D^{25} +185.63°$ (C 1.05, MeOH).

$C_{24}H_{26}N_2O_3S$ (422.54). Calcd: C, 68.23; H, 6.20; N, 6.63. Found: C, 67.82; H, 6.15; N, 6.65.

EXAMPLE 23

(+)-cis-2,3-Dihydro-3-hydroxy-5-[2-(dimethylamino)ethyl]-2-(4-methoxyphenyl)naphtho[2,1-b][1,4]thiazepin-4(5H)-one Hydrochloride Semihydrate A sample of the product of Example 22, on treatment with hydrogen chloride (anhydrous) in ethyl acetate, gave amorphous (+)-cis-2,3-dihydro-3-hydroxy-5-[2-(dimethylamino)ethyl]-2-(4-methoxyphenyl)naphtho[2,1-b][1,4]thiazepin-4(5H)-one hydrochloride semihydrate, $[\alpha]_D^{25} +175.81°$ (C 0.99, MeOH).

$C_{24}H_{26}N_2O_3S \cdot HCl \cdot 0.5H_2O$. Calcd: C, 61.59; H, 6.03; N, 5.99. Found: C, 62.03; H, 6.16; N, 6.05.

EXAMPLE 24

(−)-cis-3-(Acetyloxy)-2,3-dihydro-5-[2-(dimethylamino)ethyl]-2-(4-methoxyphenyl)naphtho[2,1-b][1,4]thiazepin-4(5H)-one To a solution of 2.5 g (0.0059 mol) of (−)-cis-2,3-dihydro-3-hydroxy-5-[2-(dimethylamino)ethyl]-2-(4-methoxyphenyl)naphtho[2,1-b][1,4]thiazepin-4(5H)-one in 25 ml of pyridine was added dropwise 1.2 g of acetyl chloride at ice-bath temperature. The mixture was stirred at ice-bath temperature for 17 hours and concentrated to dryness. The residue was partitioned between dilute ammonium hydroxide and ethyl acetate. The ethyl acetate solutions were washed with water and dried (MgSO$_4$). Removal of the solvent gave 2.7 g of product which after recrystallization from ether afforded 2.5 g (91%) of (−)-cis-3-(acetyloxy)-2,3-dihydro-5-[2-(dimethylamino)ethyl]-2-(4-methoxyphenyl)-naphtho[2,1-b][1,4]thiazepin-4(5H)-one, mp 125°–125°, $[\alpha]_D^{25} -226.37°$ (C 1.00, MeOH).

$C_{26}H_{28}N_2O_4S$ (464.56). Calcd: C, 67.22; H, 6.08; N, 6.03. Found: C, 67.09; H, 6.13; N, 6.03.

EXAMPLE 25

(−)-cis-3-(Acetyloxy)-2,3-dihydro-5-[2-(dimethylamino)ethyl]-2-(4-methoxyphenyl)naphtho[2,1-b][1,4]thiazepin-4(5H)-one (E)-2-Butenedioate 2.2 g (0.0047 mol) of the product of Example 24, on treatment with 0.55 g (0.0047 mol) of fumaric acid in acetone gave 2.1 g (76%) of (−)-cis-3-(acetyloxy)-2,3-dihydro-5-[2-(dimethylamino)ethyl]-2-(4-methoxyphenyl)naphtho[2,1-b][1,4]thiazepin-4(5H)-one (E)-2-butenedioate, mp 204°–205°, $[\alpha]_D^{25} -189.82°$ (C 1.12, MeOH).

$C_{26}H_{28}N_2O_4S \cdot C_4H_4O_4$ (580.63). Calcd: C, 62.06; H, 5.56; N, 4.83. Found: C, 62.18; H, 5.58; N, 4.84.

EXAMPLE 26

(+)-cis-3-(Acetyloxy)-2,3-dihydro-5-[2-(dimethylamino)ethyl]-2-(4-methoxyphenyl)naphtho[2,1-b][1,4]thiazepin-4(5H) one.

To a solution of 3.6 g (0.0085 mol) of (+)-cis-2,3-dihydro-3-hydroxy-5-[2-(dimethylamino)ethyl]-2-(4-methoxyphenyl)naphtho[2,1-b][1,4]thiazepin-4(5H)-one in 36 ml of pyridine was added dropwise 2.0 g of acetyl chloride at ice-bath temperature. The mixture was stirred at ice-bath temperature for 17 hours and concentrated to dryness. The residue was partitioned between dilute ammonium hydroxide and ethyl acetate. The ethyl acetate solution was washed with water and dried (MgSO$_4$). Removal of the solvent gave 3.9 g (98%) of (+)-cis-3-(acetyloxy)-2,3-dihydro-5-[2-(dimethylamino)ethyl]-2-(4-methoxyphenyl)naphtho[2,1- b][1,4]thiazepin-4(5H)-one. The analyzed sample was recrystallized from ether, mp 123°–124°, $[\alpha]_D^{25}$ +222.49° (C 1.02, MeOH).

$C_{26}H_{28}N_2O_4S$ (464.56). Calcd: C, 67.22; H, 6.08; N, 6.03. Found: C, 67.13; H, 6.17; N, 5.89.

EXAMPLE 27

(+)-cis-3-(Acetyloxy)-2,3-dihydro-5-[2-(dimethylamino)ethyl]-2-(4-methoxyphenyl)naphtho[2,1-b][1,4]thiazepin-4(5H)-one (E)-2-Butenedioate 3.8 g (0.0082 mol) of the product of Example 26, on treatment with 0.95 g (0.0081 mol) of fumaric acid in acetone gave 4.0 g (84%) of (+)-cis-3-(acetyloxy)-2,3-dihydro-5-[2-(dimethylamino)ethyl]-2-(4-methoxyphenyl)naphtho[2,1-b][1,4]thiazepin-4(5H)-one (E)-2-butenedioate. The analyzed sample was recrystallized from acetone, mp 203°–204°, $[\alpha]_D^{25}$ +190.58° (C 0.98, MeOH).

$C_{26}H_{28}N_2O_4S \cdot C_4H_4O_4$ (580.63). Calcd: C, 62.06; H, 5.56; N, 4.83. Found: C, 62.07; H, 5.49; N, 4.88.

EXAMPLE 28

(±)-cis-3-[(Ethoxycarbonyl)oxy]-2,3-dihydro-2-(4-methoxy-phenyl)-5-[2-(dimethylamino)ethyl]naphtho[2,1-b][1,4]thiazepin-4(5H)-one To a solution of 2.0 g (0.0047 mol) of (±)-cis-2,3-dihydro-3-hydroxy-5-[2-(dimethylamino)ethyl]-2-(4-methoxyphenyl)naphtho[2,1-b][1,4]thiazepin-4(5H)-one in 25 ml of pyridine (dried over KOH), chilled in an ice-bath, was added dropwise 0.65 g (0.006 mol) of ethyl chloroformate and stored in the freezer over night. The mixture was concentrated under reduced pressure and the residue was partitioned between ethyl acetate and dilute ammonium hydroxide. The ethyl acetate solution was washed with brine, then dried (MgSO4) and removal of the solvent gave 2.3 g (98%) of (±)-cis-3-[(ethoxycarbonyl)oxy]-2,3-dihydro-2-(4-methoxyphenyl)-5-[2-(dimethylamino)ethyl]naphtho[2,1-b][1,4]thiazepin-4(5H)-one. The analyzed sample was recrystallized from ether, mp 125°–126°.

$C_{27}H_{30}N_2O_5S$ (494.53). Calcd: C, 65.57; H, 6.11; N, 5.67. Found: C, 65.50; H, 6.19; N, 5.69.

EXAMPLE 29

(±)-cis-3-[(Ethoxycarbonyl)oxy]-2,3-dihydro-2-(4-methoxyphenyl)-5-[2-(dimethylamino)ethyl]naphtho[2,1-b][1,4]thiazepin-4(5H)-one (E)-2-Butenedioate 0.5 g (0.001 mol) of the product of Example 28 on treatment with 0.120 g (0.001 mol) of fumaric acid in acetone afforded 0.5 g (82%) of (±)-cis-3-[(ethoxycarbonyl)oxy]-2,3-dihydro-2-(4-methoxyphenyl)-5-[2-(dimethylamino)ethyl]naphtho[2,1-b][1,4]thiazepin-4(5H)-one (E)-2-butenedioate. The analyzed sample was recrystallized from acetone, mp 205°–206°.

$C_{27}H_{30}N_2O_5S \cdot C_4H_4O_4$ (610.66). Calcd: C, 60.97; H, 5.61; N, 4.59. Found: C, 60.96; H, 5.55; N, 4.50.

EXAMPLE 30

(±)-cis-2,3-Dihydro-3-methoxy-5-[2-(dimethylamino)ethyl]-2-(4-methoxyphenyl)naphtho[2,1-b][1,4]thiazepin-4(5H)-one To a mixture of 3.2 g (0.008 mol) of (±)-cis-2,3-dihydro-3-hydroxy-5-[2-(dimethylamino)ethyl]-2-(4-methoxyphenyl)naphtho[2,1-b][1,4]thiazepin-4(5H)-one, and 60 ml of benzene was added 0.5 g of sodium hydride (50% in mineral oil) and heated at reflux for 1 hour. After cooling to room temperature 1.3 g (0.01 mol) of dimethyl sulfate was added dropwise to the above mixture and stirred at this temperature for 17 hours. The reaction mixture was partitioned between dilute ammonium hydroxide and ethyl acetate. The organic phase was washed with brine and dried (MgSO4). Removal of the solvent gave 2.3 g of product, which after recrystallization from ethyl acetate, afforded 1.9 g (58%) of (±)-cis-2,3-dihydro-3-methoxy-5-[2-(dimethylamino)ethyl]-2-(4-methoxyphenyl)naphtho[2,1-b][1,4]thiazepin-4(5H)-one, mp 177°–178°.

$C_{25}H_{28}N_2O_3S$ (436.49). Calcd: C, 68.79; H, 6.47; N, 6.42. Found: C, 69.07; H, 6.49; N, 6.16.

EXAMPLE 31

(±)-cis-2,3-Dihydro-3-methoxy-5-[2-(dimethylamino)ethyl]-2-(4-methoxyphenyl)naphtho[2,1-b][1,4]thiazepin-4(5H)-one (E)-2-Butenedioate 0.3 g (0.0007 mol) of the product of Example 31, on treatment with 0.08 g (0.0007 mol) of fumaric acid in acetone afforded 0.3 g (79%) of (±)-cis-2,3-dihydro-3-methoxy-5-[2-(dimethylamino)ethyl]-2-(4-methoxyphenyl)naphtho[2,1-b][1,4]thiazepin-4(5H)-one (E)-2-butenedioate. The analytical sample was recrystallized from acetone, mp 242°–243°.

$C_{25}H_{28}N_2O_3S \cdot C_4H_4O_4$ (552.62). Calcd: C, 63.03; H, 5.84; N, 5.07. Found: C, 63.01; H, 5.69; N, 5.06.

EXAMPLE 32

(±)-cis-2,3-Dihydro-3-(2-methoxy-1-oxoethoxy)-2-(4-methoxyphenyl)-5-[2-(dimethylamino)ethyl]naphtho[2,1-b][1,4]thiazepin-4(5H)-one To a solution of 2.5 g (0.0059 mol) of (±)-cis-2,3-dihydro-3-hydroxy-5-[2-(dimethylamino)ethyl]-2-(4-methoxyphenyl)naphtho[2,1-b][1,4]thiazepin-4(5H)-one in 25 ml of pyridine (dried over KOH) was added dropwise at ice-bath temperature, 1.2 g (0.011 mol) of methoxyacetyl chloride and the mixture was stirred at this temperature overnight. It was concentrated at reduced pressure and the residue was partitioned between ethyl acetate and dilute ammonium hydroxide. The ethyl acetate solution was washed with brine (50 ml) and dried (MgSO4). Removal of the solvent gave 2.7 g of product, which after recrystallization from ether, afforded 2.2 g (76%) of (±)-cis-2,3-dihydro-3-(2-methoxy-1-oxoethoxy)-2-(4-methoxyphenyl)-5-(dimethylamino)ethyl]naphtho[2,1-b][1,4]thiazepin-4(5H)-one, mp 131°–132°.

$C_{27}H_{30}N_2O_5S$ (494.60). Calcd: C, 65.57; H, 6.11; N, 5.66. Found: C, 65.36; H, 6.29; N, 5.44.

EXAMPLE 33

(±)-cis-2,3-Dihydro-3-(2-methoxy-1-oxoethoxy)-2-(4-methoxyphenyl)-5-[2-(dimethylamino)ethyl]naphtho[2,1-b][1,4]thiazepin-4(5H)-one (E)-2-Butenedioate 1.7 g (0.0034 mol) of the product of Example 32, on treatment with 0.4 g (0.0034 mol) of fumaric acid in acetone afforded 1.6 g (77%) of (±)-cis-2,3-dihydro-3-(2-methoxy-1-oxoethoxy)-2-(4-methoxyphenyl)-5-[2-(dimethylamino)ethyl]naphtho[2,1-b][1,4]thiazepin-4(5H)one (E)-2-butenedioate. The analytical sample was recrystallized from acetone, mp 217°–218°.

$C_{27}H_{30}N_2O_5S \cdot C_4H_4O_4$ (610.68). Calcd: C, 60.97; H, 5.61; N, 4.59. Found: C, 60.96; H, 5.84; N, 4.62.

EXAMPLE 34

(±)-cis-3-[(Cyclopropylcarbonyl)oxy]-2,3-dihydro-5-[2-(dimethylamino)ethyl]-2-(4-methoxyphenyl)naphtho[2,1-b][1,4]thiazepin-4(5H)-one To a solution of 2.5 g (0.0059 mol) of (±)-cis-2,3-dihydro-3-hydroxy-5-[2-(dimethylamino)ethyl]-2-(4-methoxyphenyl)naphtho[2,1-b][1,4]thiazepin-4(5H)-one in 25 ml pyridine was added dropwise 1.2 g (0.011 mol) of cyclopropanecarboxylic acid chloride at ice-bath temperature. The solution was kept in the freezer for 17 hours and concentrated under reduced pressure. The residue was partitioned between dilute ammonium hydroxide and ethyl acetate. The organic solution was washed with brine and dried ($MgSO_4$). Removal of the solvent gave 3.0 g of product, which was recrystallized from ether to afford 2.4 g (83%) of (±)-cis-3-[(cyclopropylcarbonyl)oxy]-2,3-dihydro-5-[2-(dimethylamino)ethyl]-2-(4-methoxyphenyl)naphtho[2,1-b][1,4]-thiazepin-4(5H)-one, mp, 160°–161°.

$C_{28}H_{30}N_2O_4S$ (490.54). Calcd: C, 68.55; H, 6.16; N, 5.71. Found: C, 68.44; H, 6.08; N, 5.59.

EXAMPLE 35

(±)-cis-3-[(Cyclopropylcarbonyl)oxy]-2,3-dihydro-5-[2-(dimethylamino)ethyl]-2-(4-methoxyphenyl)naphtho[2,1-b][1,4]thiazepin-4(5H)-one (E)-2-Butenedioate 2.4 g (0.005 mol) of the product of Example 35, on treatment with 0.6 g (0.0049 mol) of fumaric acid in acetone afforded 2.5 g (84%) of (±)-cis-3-[(cyclopropylcarbonyl)oxy]-2,3-dihydro-5-[2-(dimethylamino)ethyl]-2-(4-methoxyphenyl)naphtho[2,1-b][1,4]thiazepin-4(5H)-one (E)-2-butenedioate. The analytical sample was recrystallized from methanol, mp 242°–243°.

$C_{28}H_{30}N_2O_4S \cdot C_4H_4O_4$ (606.67). Calcd: C, 63.36; H, 5.65; N, 4.62. Found: C, 63.45; H, 5.64; N, 4.55.

EXAMPLE 36 cis-rac-5-[2-(Dimethylamino)propyl]-2,3-dihydro-3-hydroxy-2-(4-methoxyphenyl)naphtho[2,1-b][1,4]thiazepin-4(5H)-one A mixture of 4.4 g (0.013 mol) of (±)-cis-2,3-dihydro-3-hydroxy-2-(4-methoxyphenyl)naphtho[2,1-b][1,4]thiazepin-4(5H)-one, 2.0 g of powdered potassium carbonate and 1.7 g of 3-dimethylaminopropyl chloride in 100 ml of ethyl acetate was stirred and heated at reflux for two hours, then an additional 0.9 g of 3-dimethylaminopropyl chloride was added three times at two hour intervals. The mixture was heated at reflux for a total of 12 hours, then cooled to room temperature and diluted with 100 ml of water. The organic phase was separated, washed with brine and dried ($MgSO_4$). Removal of the solvent gave the product, which after crystallization from ether provided 2.3 g (43%) of cis-rac-5-[2-(dimethylamino)propyl]-2,3-dihydro-3-hydroxy-2-(4-methoxyphenyl)naphtho[2,1-b][1,4]thiazepin-4(5H)-one, mp 136°–137°.

$C_{25}H_{28}N_2O_3S$ (436.39). Calcd: C, 68.79; H, 6.47; N, 6.42. Found: C, 68.60; H, 6.43; N, 6.18.

EXAMPLE 37 cis-rac-5-[3-(Dimethylamino)propyl]-2,3-dihydro-3-hydroxy-2-(4-methoxyphenyl)naphtho[2,1-b][1,4]thiazepin-4(5H)-one (E)-2-Butenedioate 1.0 g (0.0023 mole) of the product of Example 36, on treatment with 0.3 g (0.0025 mol) of fumaric acid in acetone afforded 1.1 g (87%) of cis-rac-5-[3-(dimethylamino)propyl]-2,3-dihydro-3-hydroxy-2-(4-methoxyphenyl)naphtho[2,1-b][1,4]thiazepin-4(5H)-one (E)-2-butenedioate, mp 227°–228°.

$C_{25}H_{28}N_2O_3 \cdot C_4H_4O_4$ (552.56). Calcd: C, 63.03; H, 5.84; N, 5.07. Found: C, 63.04; H, 5.96; N, 4.89.

EXAMPLE 38 cis-rac-3-(Acetyloxy)-2,3-dihydro-2-(4-methoxyphenyl)-5-[3-(dimethylamino)propyl]naphtho[2,1-b][1,4]thiazepin-4(5H)-one To a solution of 1.4 g (0.0032 mol) of (±)-cis-5-[3-(dimethylamino)propyl]-2,3-dihydro-3-hydroxy-2-(4-methoxypheny)naphtho[2,1-b][1,4]thiazepin-4(5H)-one in 25 ml pyridine (dried over KOH) was added dropwise at ice-bath temperature 1.0 g of acetyl chloride and the mixture was kept at this temperature overnight. It was concentrated at reduced pressure and the residue was partitioned between ethyl acetate and dilute ammonium hydroxide. The combined ethyl acetate solutions were washed with brine and dried ($MgSO_4$). Removal of the solvent gave the product, which after crystallization from ethyl acetate, afforded 1.3 g (87%) of cis-rac-3-(acetyloxy)-2,3-dihydro-2-(4-methoxyphenyl)-5-[3-(dimethylamino)propyl]naphtho[2,1-b][1,4]thiazepin-4(5H)-one, mp 154°–155°.

$C_{27}H_{30}N_2O_4S$ (478.59). Calcd: C, 67.76; H, 6.32; N, 5.85. Found: C, 67.53; H, 6.55; N, 5.83.

EXAMPLE 39 cis-rac-3-(Acetyloxy)-2,3-dihydro-2-(4-methoxyphenyl)-5-[3-(dimethylamino)propyl]naphtho[2,1-b][1,4]thiazepin-4(5H)-one (E)-2-Butenedioate To 1.3 g (0.0027 mole) of the product of Examples 38, in acetone (25 ml) was added 0.3 g (0.0026 mol) of fumaric acid and resulting crystals were collected to give 1.3 g (81%) of cis-rac-3-(acetyloxy)-2,3-dihydro-2-(4-methoxyphenyl)-5-[3-(dimethylamino)propyl]naphtho[2,1-b][1,4]thiazepin-4(5H)-one (E)-2-butenedioate, mp 132°–134°.

$C_{27}H_{30}N_2O_4S \cdot C_4H_4O_4$ (594.66). Calcd: C, 62.62; H, 5.76; N, 4.71. Found: C, 62.40; H, 5.98; N, 4.67.

EXAMPLE 40 cis-rac-5-[2-(Diethylamino)ethyl]-2,3-dihydro-3-hydroxy-2-(4-methoxyphenyl)naphtho[2,1-b][1,4]thiazepin-4(5H)-one (E)-Butenedioate A mixture of 4.4 g (0.013 mol) of cis-rac-2,3-dihydro-3-hydroxy-2-(4-methoxyphenyl)naphtho[2,1-b][1,4]thiazepin-4(5H)-one, 2.0 g of powdered potassium carbonate and 1.8 g of diethylaminoethyl chloride in 100 ml of ethyl acetate was stirred and heated at reflux for 2 hours, then an additional 0.5 g of 2-diethylaminoethyl chloride was added three times at 2 hour intervals. The mixture was heated at reflux for a total of 12 hours, then cooled to room temperature and diluted with water (100 ml). The organic phase was separated, washed with brine and dried ($MgSO_4$). Removal of the solvent gave 5.4 g of the title product, which in acetone was treated with 1.3 g of fumaric acid. The resulting crystals were collected and dried to give 3.7 g (52%) of rac-cis-5-[2-(diethylamino)ethyl]-2,3-dihydro-3-hydroxy-2-(4-methoxyphenyl)naphtho[2,1-b][1,4]thiazepin-4(5H)-one (E)-butenedioate, mp 195°–196°.

$C_{26}H_{30}N_2O_3S \cdot C_4H_4O_4$ (566.65). Calcd: C, 63.59; H, 6.05; N, 4.94. Found: C, 63.53; H, 6.08; N, 5.04.

EXAMPLE 41 cis-rac-5-[2-(Diethylamino)ethyl]-2,3-dihydro-3-hydroxy-2-(4-methoxyphenyl)naphtho[2,1-b][1,4]thiazepin-4-(5H)-one A sample of the above (E)-2-butenedioate salt of Example 40, in water was treated with concentrated ammonium hydroxide and the aqueous suspension was extracted with ethyl acetate. The ethyl acetate solutions were washed with brine and dried (MgSO$_4$). Removal of the solvent gave the base, which after crystallization from ether afforded cis-rac-5-[2-(diethylamino)ethyl]-2,3-dihydro-3-hydroxy-2-(4-methoxyphenyl)naphtho[2,1-b][1,4]thiazepin-4(5H)-one, mp 111°–112°.

$C_{26}H_{30}N_2O_3S$ (450.51). Calcd: C, 69.31; H, 6.71; N, 6.22. Found: C, 69.04; H, 6.76; N, 6.27.

EXAMPLE 42 cis-rac-3-(Acetyloxy)-5-[2-(diethylamino)ethyl]-2,3-dihydro-2-(4-methoxyphenyl)naphtho[2,1-b][1,4]thiazepin-4(5H)-one (E)-2-Butenedioate A solution of 1.9 g (0.0042 mole) of cis-rac-5-[2-(diethylamino)ethyl]-2,3-dihydro-3-hydroxy-2-(4-methoxyphenyl)naphtho[2,1-b][1,4]thiazepin-4(5H)-one in 25 ml acetone was acidified by hydrogen chloride (anhydrous) and then concentrated to dryness under reduced pressure. The residue was dissolved in 25 ml of acetic anhydride, stirred and heated at 100° for 17 hours. The excess reagent was removed under reduced pressure and the residue was dissolved in water. The aqueous suspension was made basic with concentrated ammonium hydroxide and extracted with ethyl acetate (3×75 ml). The combined ethyl acetate solutions were washed with brine (50 ml) and dried (MgSO$_4$). Removal of the solvent gave 1.8 g of the title product, which in acetone was treated with furmaric acid (0.4 g). The crystals were separated and dried to give 1.2 g (46%) of cis-rac-3-(acetyloxy)-5-[2-(diethylamino)ethyl]-2,3-dihydro-2-(4-methoxyphenyl)naphtho[2,1-b][1,4]thiazepin-4(5H)-one (E)-2-butenedioate, mp 180°–181°.

$C_{26}H_{32}N_2O_4S \cdot C_4H_4O_4$ (608.62). Calcd: C, 63.15; H, 5.96; N, 4.61. Found: C, 63.24; H, 6.20; N, 4.75.

EXAMPLE 43 cis-rac-3-(Acetyloxy)-5-[2-(diethylamino)ethyl]-2,3-dihydro-2-(4-methoxyphenyl)naphtho[2,1-b][1,4]thiazepin-4(5H)-one A sample of the (E)-2-butenedioate salt of Example 42, in water was treated with concentrated ammonium hydroxide and the aqueous suspension was extracted with ethyl acetate. The ethyl acetate solutions were washed with brine and dried (MgSO$_4$). Removal of the solvent gave the base of Example 42, which after crystallization from ether afforded cis-rac-3-(acetyloxy)-5-[2-(diethylamino)ethyl]-2,3-dihydro-2-(4-methoxyphenyl)naphtho[2,1-b][1,4]thiazepin-4(5H)-one, mp 112°–113°.

$C_{28}H_{32}N_2O_4S$ (492.61). Calcd: C, 68.27; H, 6.55; N, 5.69. Found: C, 68.59; H, 6.61; N, 5.70.

EXAMPLE 44—TABLETS

| Item | Ingredient | mg/tablet 100 mg | mg/tablet 200 mg |
|---|---|---|---|
| 1. | cis-(+)-3-(Acetyloxy)-2,3-dihydro-5-[2-(dimethylamino)ethyl]-2-(4-methoxyphenyl)naphtho[2,1-b][1,4]thiazepin 4(5H)—one (E)-2-butenedioate | 100 | 200 |
| 2. | Lactose | 100 | 200 |
| 3. | Polyvinylpyrrolidone (PVP) | 10 | 20 |
| 4. | Modified Starch | 10 | 20 |
| 5. | Magnesium Stearate | 3 | 6 |
|   |   | 223 mg | 446 mg |

(1) Mix Items 1, 2 and 4 and granulate with PVP in water or alcohol.
(2) Dry the granulation at 45° C.
(3) Mill the dried granulation through a suitable mill.
(4) Add Item 5 and mix for three minutes and compress on a suitable press.

EXAMPLE 45—CAPSULES

| Item | Ingredient | mg/tablet 100 mg | mg/tablet 200 mg |
|---|---|---|---|
| 1. | cis-(+)-3-(Acetyloxy)-2,3-dihydro-5-[2-(dimethylamino)ethyl]-2-(4-methoxyphenyl)-naphtho[1,2-b][1,4]thiazepin-4(5H)—one (E)-2-butenedioate | 100 | 200 |
| 2. | Corn Starch (Pregelatinized) | 50 | 80 |
| 3. | Modified Starch | 10 | 20 |
| 4. | Talc | 20 | 20 |
| 5. | Magnesium Stearate | 1 | 1 |
|   |   | 181 mg | 322 mg |

(1) Mix Items 1–3 and wet granulate with water. Dry at 45° C. overnight.
(2) Mill through suitable screen using appropriate milling equipment.
(3) Add Items 4 and 5 and mix for five minutes.
(4) Fill into suitable capsule.

EXAMPLE 46—PARENTERAL SOLUTION

| Item | Ingredient | mg/ml |
|---|---|---|
| 1. | cis-rac-2,3-Dihydro-3-hydroxy-5-[2-(dimethylamino)ethyl]-2-(4-methoxyphenyl)naphtho[2,1-b][1,4]thiazepin-4(5H)—one hydrochloride | 10 |
| 2. | Benzyl Alcohol | 10 |
| 3. | Sorbitol | 38 |
| 4. | Hydrochloric Acid q.s. to pH | 3–7 |
| 5. | Sodium Hydroxide q.s. to pH | 3–7 |
| 6. | Water for Injection q.s. to | 1 ml |

In the above parenteral solution q.s. means sufficient quantity.

We claim:
1. A compound of the formula:

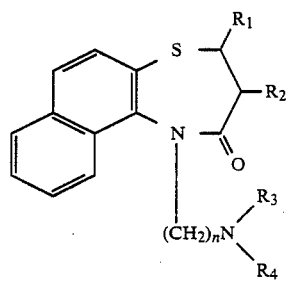

I wherein R$_1$ is phenyl substituted with 1 to 3 substituents selected from the group consisting of lower alkoxy and halogen; R$_2$ is hydroxy, lower alkoxy, lower alkanoyloxy, lower cycloalkylcarbonyloxy,

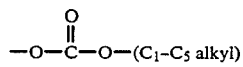

or

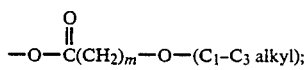

R$_3$ and R$_4$ are independently lower alkyl, phenyl lower alkyl, or together form a piperidine or pyrrolidine ring; n is 2 to 4; m is 1 to 2; or a pharmaceutically acceptable acid addition salt thereof.

2. A compound in accordance with claim 1, of the formula

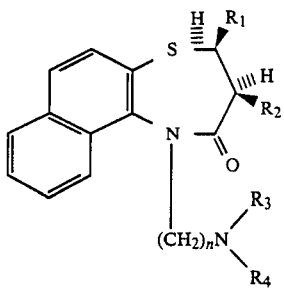

wherein R$_1$ is phenyl substituted with 1 to 3 substituents selected from the group consisting of lower alkoxy and halogen; R$_2$ is hydroxy, lower alkoxy, lower alkanoyloxy, lower cycloalkylcarbonyloxy,

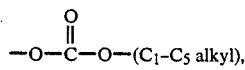

or

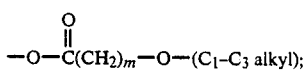

R$_3$ and R$_4$ are independently lower alkyl, phenyl lower alkyl or together form a piperidine or pyrrolidine ring; n is 2 to 4; m is 1 to 2; an enantiomer or a racemate thereof or a pharmaceutically acceptable acid addition salt thereof.

3. A compound in accordance with claim 2, of the formula

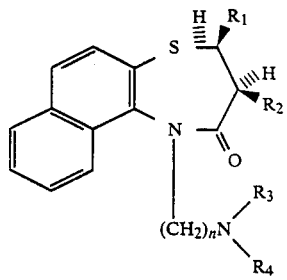

wherein R$_1$ is phenyl substituted with 1 to 3 substituents selected from the group consisting of lower alkoxy and halogen; R$_2$ is hydroxy, lower alkoxy, lower alkanoyloxy, lower cycloalkylcarbonyloxy,

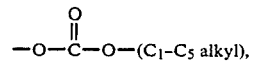

or

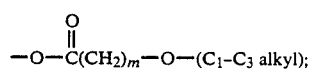

R$_3$ and R$_4$ are independently lower alkyl, phenyl lower alkyl or together form a piperidine or pyrrolidine ring; n is 2 to 4; m is 1 to 2; or a pharmaceutically acceptable acid addition salt thereof.

4. A compound in accordance with claim 2, wherein R$_1$ is 4-lower alkoxyphenyl and R$_2$ is hydroxy.

5. A compound in accordance with claim 4, wherein R$_1$ is 4-methoxyphenyl, R$_3$ and R$_4$ are independently lower alkyl and n is 2 to 3.

6. A compound in accordance with claim 5, cis-rac-2,3-dihydro-3-hydroxy-5-[2-(dimethylamino)ethyl]-2-(4-methoxyphenyl)naphtho[2,1-b][1,4]thiazepin-4(5H)-one or the hydrochloride salt thereof.

7. A compound in accordance with claim 3, wherein R$_1$ is 4-lower alkoxyphenyl and R$_2$ is hydroxy.

8. A compound in accordance with claim 7, wherein R$_1$ is 4-methoxyphenyl, R$_3$ and R$_4$ are independently lower alkyl, and n is 2 to 3.

9. A compound in accordance with claim 8, cis-(+)-2,3-dihydro-3-hydroxy-5-[2-(dimethylamino)ethyl]-2-(4-methoxyphenyl)naphtho[2,1-b][1,4]thiazepin-4(5H)-one or the hydrochloride salt thereof.

10. A compound in accordance with claim 2, wherein R$_1$ is 4-lower alkoxyphenyl and R$_2$ is selected from the group consisting of acetyloxy and propionyloxy.

11. A compound in accordance with claim 10, wherein R$_1$ is 4-methoxyphenyl, R$_2$ is acetyloxy, R$_3$ and R$_4$ are independently lower alkyl, and n is 2 to 3.

12. A compound in accordance with claim 11, cis-rac-3-(acetyloxy)-2,3-dihydro-5-[2-(dimethylamino)ethyl]-2-(4-methoxyphenyl)naphtho[2,1-b][1,4]thiazepin-4(5H)-one, or the (E)-2-butenedioate salt thereof.

13. A compound in accordance with claim 11, cis-(−)-3-(acetyloxy)-2,3-dihydro-5-[2-(dimethylamino)ethyl]-2-(4-methoxyphenyl)naphtho[2,1-b][1,4]thiazepin-4(5H)-one, or the (E)-2-butenedioate salt thereof.

14. A compound in accordance with claim 3, wherein R$_1$ is 4-lower alkoxyphenyl and R$_2$ is selected from the group consisting of acetyloxy and propionyloxy.

15. A compound in accordance with claim 14, wherein R$_1$ is 4-methoxyphenyl, R$_2$ is acetyloxy, R$_3$ and R$_4$ are independently lower alkyl, and n is 2 to 3.

16. A compound in accordance with claim 15, cis-(+)-3-(acetyloxy)-2,3-dihydro-5-[2-(dimethylamino)ethyl]-2-(4-methoxyphenyl)naphtho[2,1-b][1,4]thiazepin-4(5H)-one, or the (E)-2-butenedioate salt thereof.

17. A compound in accordance with claim 2, wherein R$_1$ is 4-lower alkoxyphenyl and R$_2$ is

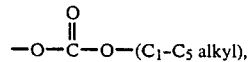

18. A compound in accordance with claim 17, cis-(±)-[(ethoxycarbonyl)oxy])-2,3-dihydro-2-(4-methoxyphenyl)-5-[2-(dimethylamino)ethyl]naphtho[2,1-b][1,4]thiazepin-4(5H)-one, or the (E)-2-butenedioate salt thereof.

19. A compound in accordance with claim 2, wherein $R_1$ is 4-lower alkoxyphenyl and $R_2$ is lower alkoxy.

20. A compound in accordance with claim 19, cis-(±)-2,3-dihydro-3-methoxy-5-[2-(dimethylamino)ethyl]-2-(4-methoxyphenyl)naphtho[2,1-b][1,4]thiazepin-4(5H)-one, or the (E)-2-butenedioate salt thereof.

21. A compound in accordance with claim 2, wherein $R_1$ is 4-lower alkoxyphenyl and $R_2$ is lower cycloalkylcarbonyloxy.

22. A compound in accordance with claim 21, cis-(±)-3-[(cyclopropylcarbonyl)oxy]-2,3-dihydro-5-[2-(dimethylamino)ethyl]-2-(4-methoxyphenyl)naphtho[2,1-b][1,4]thiazepin-4(5H)-one, or the (E)-2-butenedioate salt thereof.

23. A compound in accordance with claim 1 of the formula:

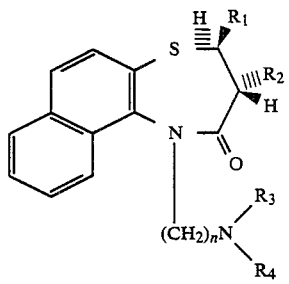

I''' wherein $R_1$ is phenyl substituted with 1 to 3 substituents selected from the group consisting of lower alkoxy and halogen; $R_2$ is hydroxy, lower alkoxy, lower alkanoyloxy, lower cycloalkylcarbonyloxy,

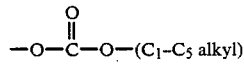

or

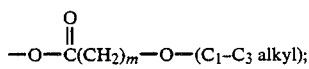

$R_3$ and $R_4$ are independently lower alkyl, phenyl lower alkyl, or together form a piperidine or pyrrolidine ring; n is 2 to 4; m is 1 to 2; an enantiomer or a racemate thereof or a pharmaceutically acceptable acid addition salt thereof.

24. A compound in accordance with claim 23, trans-rac-3-(acetyloxy)-2,3-dihydro-5-[2-(dimethylamino)ethyl]-2-(4-methoxyphenyl)naphtho[2,1-b][1,4]thiazepin-4(5H)-one or the (E)-2-butenedioate salt thereof.

25. A compound of the formula:

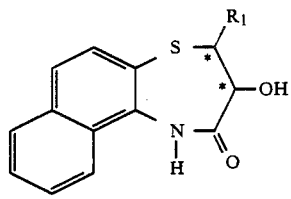

VI wherein $R_1$ is phenyl substituted with 1 to 3 substituents selected from the group consisting of lower alkoxy and halogen.

26. A compound in accordance with claim 25, of the formula

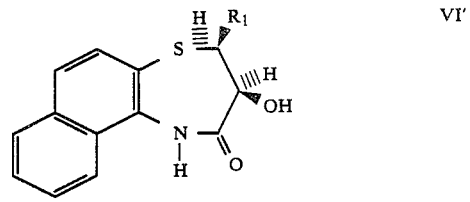

VI' wherein $R_1$ is phenyl substituted with 1 to 3 substituents selected from the group consisting of lower alkoxy and halogen; an enantiomer or a racemate thereof.

27. A compound in accordance with claim 26, wherein $R_1$ is 4-lower alkoxy phenyl.

28. A compound in accordance with claim 26, cis-rac-2,3-dihydro-3-hydroxy-2-(4-methoxyphenyl)naphtho[2,1-b][1,4]thiazepin-4(5H)-one.

29. A composition which calcium antagonist activity comprising an effective amount of a compound of the formula

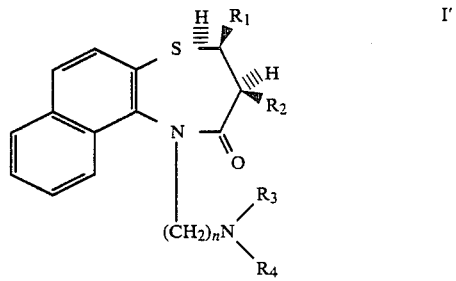

I' wherein $R_1$ is phenyl substituted with 1 to 3 substituents selected from the group consisting of lower alkoxy and halogen; $R_2$ is hydroxy, lower alkoxy, lower alkanoyloxy, lower cycloalkylcarbonyloxy,

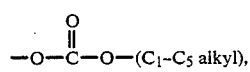

or

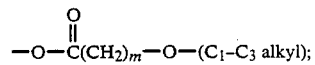

$R_3$ and $R_4$ are independently lower alkyl, or together form a piperidine or pyrrolidine ring; n is 2 to 4; m is 1 to 2; or a pharmaceutically acceptable acid addition salt thereof, and a pharmaceutically inert carrier material.

30. A composition in accordance with claim 29, comprising a compound of the formula

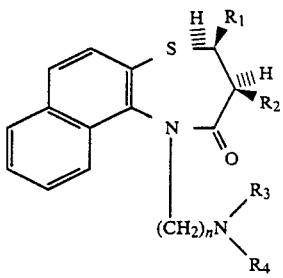

wherein R₁ is phenyl substituted with 1 to 3 substituents selected from the group consisting of lower alkoxy and halogen; R₂ is hydroxy, lower alkoxy, lower alkanoyloxy, lower cycloalkylcarbonyloxy,

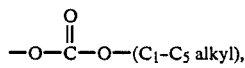

or

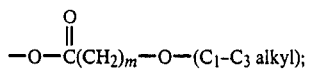

R₃ and R₄ are independently lower alkyl, or together form a piperidine or pyrrolidine ring; n is 2 to 4; m is 1 to 2; an enantiomer or a racemate thereof or a pharmaceutically acceptable acid addition salt thereof.

31. A composition in accordance with claim 30, wherein R₁ is 4-lower alkoxyphenyl and R₂ is selected from the group consisting of acetyloxy and propionyloxy.

32. A composition in accordance with claim 30, wherein the compound of the formula I is cis-(+)-2,3-dihydro-3-hydroxy-5-[2-(dimethylamino)ethyl]-2-(4-methoxyphenyl)naphtho[1,2-b][1,4]thiazepin-4(5H)-one, or the hydrochloride salt thereof.

33. A composition in accordance with claim 30, wherein the compound of the formula I is cis-(+)-3-(acetyloxy)-2,3-dihydro-5-[2-(dimethylamino)ethyl]-2-(4-methoxyphenyl)naphtho[1,2-b][1,4]thiazepin-4(5H)-one, or the (E)-2-butenedioate salt thereof.

34. A method of inducing calcium antagonist activity which comprises administering to a warm-blooded animal in need of such treatment, an effective amount of a compound of the formula

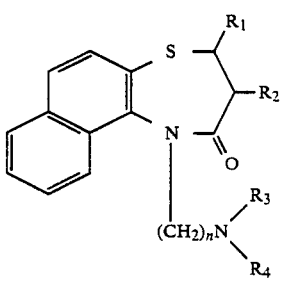

wherein R₁ is phenyl substituted with 1 to 3 substituents selected from the group consisting of lower alkoxy and halogen; R₂ is hydroxy, lower alkoxy, lower alkanoyloxy, lower cycloalkylcarbonyloxy,

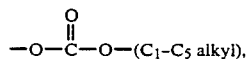

or

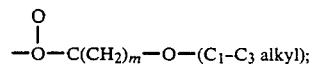

R₃ and R₄ are independently lower alkyl, phenyl lower alkyl, or together form a piperidine or pyrrolidine ring; n is 2 to 4; m is 1 to 2; or a pharmaceutically acceptable acid addition thereof.

35. A method in accordance with claim 34, which comprises administering a compound of the formula

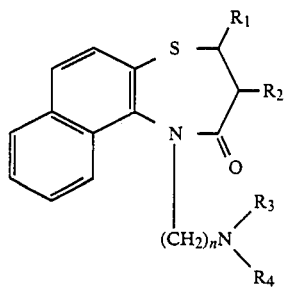

wherein R₁ is phenyl substituted with 1 to 3 substituents selected from the group consisting of lower alkoxy and halogen; R₂ is hydroxy, lower alkoxy, lower alkanoyloxy, lower cycloalkylcarbonyloxy,

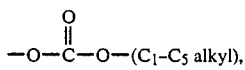

or

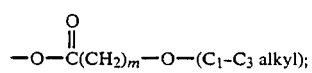

R₃ and R₄ are independently lower alkyl, phenyl lower alkyl, or together form a piperidine or pyrrolidine ring; n is 2 to 4; m is 1 to 2; or a racemate thereof, or a pharmaceutically acceptable acid addition salt thereof.

36. A method in accordance with claim 35, wherein R₁ is 4-lower alkoxyphenyl and R₂ is selected from the group consisting of acetyloxy and propionyloxy.

37. A method in accordance with claim 35, wherein the compound of formula I is cis-(+)-2,3-dihydro-3-hydroxy-5-[2-(dimethylamino)ethyl]-2-(4-methoxyphenyl)naphtho[1,2-b][1,4]thiazepin-4(5H)-one, or the hydrochloride salt thereof.

38. A method in accordance with claim 36, wherein the compound of formula I is cis-(+)-3-(acetyloxy)-2,3-dihydro-5-[2-(dimethylamino)ethyl]-2-(4-methoxyphenyl)naphtho[1,2-b][1,4]thiazepin-4(5H)-one, or the (E)-2-butenedioate salt thereof.

* * * * *